(12) United States Patent
Lundquist et al.

(10) Patent No.: US 7,995,202 B2
(45) Date of Patent: Aug. 9, 2011

(54) METHODS AND SYSTEMS FOR SIMULTANEOUS REAL-TIME MONITORING OF OPTICAL SIGNALS FROM MULTIPLE SOURCES

(75) Inventors: Paul Lundquist, San Jose, CA (US); Denis Zaccarin, San Jose, CA (US); Yves Lacroix, San Jose, CA (US); Mark Maxham, Redwood City, CA (US); Mathieu Foquet, Redwood City, CA (US); Stephen Turner, Menlo Park, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 678 days.

(21) Appl. No.: 11/704,689

(22) Filed: Feb. 9, 2007

(65) Prior Publication Data
US 2008/0030628 A1    Feb. 7, 2008

Related U.S. Application Data

(63) Continuation-in-part of application No. 11/483,413, filed on Jul. 7, 2006.

(60) Provisional application No. 60/772,908, filed on Feb. 13, 2006.

(51) Int. Cl.
*G01J 3/30* (2006.01)
(52) U.S. Cl. ........................................ 356/317
(58) Field of Classification Search .......... 356/317–318, 356/417; 250/458.1–461.2
See application file for complete search history.

(56) References Cited

U.S. PATENT DOCUMENTS

| 4,626,684 | A | | 12/1986 | Landa |
|---|---|---|---|---|
| 5,239,178 | A | | 8/1993 | Derndinger et al. |
| 5,470,710 | A | | 11/1995 | Weiss et al. |
| 5,545,531 | A | | 8/1996 | Rava et al. |
| 5,547,839 | A | | 8/1996 | Dower et al. |
| 5,578,832 | A | | 11/1996 | Trulson et al. |
| 5,631,734 | A | | 5/1997 | Stern et al. |
| 5,677,196 | A | | 10/1997 | Herron et al. |
| 5,695,934 | A | | 12/1997 | Brenner |
| 5,744,305 | A | | 4/1998 | Fodor et al. |
| 5,817,462 | A | * | 10/1998 | Garini et al. ............... 435/6 |
| 5,821,058 | A | | 10/1998 | Smith et al. |
| 5,837,858 | A | | 11/1998 | Brennan |

(Continued)

FOREIGN PATENT DOCUMENTS

EP    1105529 B1    11/2005

(Continued)

OTHER PUBLICATIONS

M.J. Levene, et al. (Jan. 31, 2003) "Zero-mode Waveguides for Single-molecule Analysis at High Concentrations." Science, 299: 682-686.

(Continued)

*Primary Examiner* — Kara E Geisel
(74) *Attorney, Agent, or Firm* — Robert H. Reamey

(57) ABSTRACT

Methods and systems for real-time monitoring of optical signals from arrays of signal sources, and particularly optical signal sources that have spectrally different signal components. Systems include signal source arrays in optical communication with optical trains that direct excitation radiation to and emitted signals from such arrays and image the signals onto detector arrays, from which such signals may be subjected to additional processing.

8 Claims, 15 Drawing Sheets

U.S. PATENT DOCUMENTS

| | | | |
|---|---|---|---|
| 5,874,219 A | 2/1999 | Rava et al. | |
| 6,071,748 A | 6/2000 | Modlin et al. | |
| 6,160,618 A * | 12/2000 | Garner | 356/318 |
| 6,210,896 B1 | 4/2001 | Chan | |
| 6,236,945 B1 | 5/2001 | Simpson et al. | |
| 6,263,286 B1 | 7/2001 | Gilmanshin et al. | |
| 6,388,788 B1 | 5/2002 | Harris et al. | |
| 6,403,970 B1 | 6/2002 | Hung | |
| 6,455,861 B1 | 9/2002 | Hoyt | |
| 6,597,450 B1 | 7/2003 | Andrews et al. | |
| 6,603,537 B1 | 8/2003 | Dietz et al. | |
| 6,686,582 B1 | 2/2004 | Volcker et al. | |
| 6,690,002 B2 | 2/2004 | Kuroda et al. | |
| 6,699,655 B2 | 3/2004 | Nikiforov | |
| 6,760,105 B2 | 7/2004 | Oshida et al. | |
| 6,784,982 B1 | 8/2004 | Blumenfeld et al. | |
| 6,800,860 B2 | 10/2004 | Dietz et al. | |
| 6,818,395 B1 | 11/2004 | Quake et al. | |
| 6,867,851 B2 | 3/2005 | Blumenfeld et al. | |
| 6,869,764 B2 | 3/2005 | Williams et al. | |
| 6,917,726 B2 | 7/2005 | Levene et al. | |
| 6,919,211 B1 | 7/2005 | Fodor et al. | |
| 6,979,830 B2 | 12/2005 | Dietz et al. | |
| 6,982,146 B1 | 1/2006 | Schneider et al. | |
| 7,008,766 B1 | 3/2006 | Densham | |
| 7,033,762 B2 | 4/2006 | Nelson et al. | |
| 7,033,764 B2 | 4/2006 | Korlach et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,064,197 B1 | 6/2006 | Rabbani et al. | |
| 7,081,954 B2 | 7/2006 | Sandstrom | |
| 7,083,914 B2 | 8/2006 | Seul et al. | |
| 7,130,041 B2 | 10/2006 | Bouzid et al. | |
| 7,135,667 B2 | 11/2006 | Oldham et al. | |
| 7,139,074 B2 | 11/2006 | Reel | |
| 7,145,645 B2 | 12/2006 | Blumenfeld et al. | |
| 7,170,597 B1 | 1/2007 | Hooper et al. | |
| 7,189,361 B2 | 3/2007 | Carson et al. | |
| 7,199,357 B1 | 4/2007 | Oldham et al. | |
| 7,209,836 B1 | 4/2007 | Schermer et al. | |
| 7,227,128 B2 | 6/2007 | Sagatelyan | |
| 7,233,393 B2 | 6/2007 | Tomaney et al. | |
| 7,292,742 B2 | 11/2007 | Levene et al. | |
| 7,302,146 B2 | 11/2007 | Turner et al. | |
| 7,302,348 B2 | 11/2007 | Ghosh et al. | |
| 7,323,681 B1 | 1/2008 | Oldham et al. | |
| 2001/0033374 A1 | 10/2001 | Hoyt | |
| 2001/0046050 A1 | 11/2001 | Hoyt | |
| 2002/0008148 A1 | 1/2002 | Empedocles et al. | |
| 2003/0044781 A1 | 3/2003 | Korlach et al. | |
| 2003/0077610 A1 | 4/2003 | Nelson et al. | |
| 2003/0087282 A1 | 5/2003 | Oshida et al. | |
| 2003/0103207 A1 | 6/2003 | Kopf-Sill et al. | |
| 2003/0112432 A1 | 6/2003 | Yguerabide et al. | |
| 2003/0151735 A1 | 8/2003 | Blumenfeld et al. | |
| 2003/0174324 A1 | 9/2003 | Sandstrom | |
| 2003/0174992 A1 | 9/2003 | Levene et al. | |
| 2003/0175987 A1 | 9/2003 | Verdonk et al. | |
| 2003/0186276 A1 | 10/2003 | Odera | |
| 2003/0190647 A1 | 10/2003 | Odera | |
| 2003/0194740 A1 | 10/2003 | Williams | |
| 2003/0215862 A1 | 11/2003 | Parce et al. | |
| 2004/0038390 A1 | 2/2004 | Boege et al. | |
| 2004/0048301 A1 | 3/2004 | Sood et al. | |
| 2004/0197816 A1 | 10/2004 | Empedocles et al. | |
| 2004/0224319 A1 | 11/2004 | Sood et al. | |
| 2005/0135974 A1 | 6/2005 | Harvey et al. | |
| 2005/0206895 A1 | 9/2005 | Salmelainen | |
| 2006/0007439 A1 | 1/2006 | Corcoran | |
| 2006/0040379 A1 | 2/2006 | Tanaami | |
| 2006/0152727 A1 | 7/2006 | Bickmore et al. | |
| 2007/0048748 A1 | 3/2007 | Williams et al. | |
| 2007/0099212 A1 | 5/2007 | Harris | |
| 2007/0114362 A1 | 5/2007 | Feng et al. | |
| 2007/0178012 A1 | 8/2007 | Ferrante et al. | |
| 2007/0206187 A1 | 9/2007 | Lundquiist et al. | |
| 2008/0020938 A1 | 1/2008 | Kaplan | |

FOREIGN PATENT DOCUMENTS

| | | |
|---|---|---|
| WO | WO 91/06678 | 5/1991 |
| WO | WO 96/27025 | 9/1996 |
| WO | WO 99/05315 | 2/1999 |
| WO | WO 00/36152 | 6/2000 |
| WO | WO 01/16375 A2 | 3/2001 |
| WO | WO 2004/100068 A2 | 11/2004 |
| WO | WO 2006/116726 A2 | 2/2006 |
| WO | WO 2006/135782 A2 | 12/2006 |
| WO | WO 2007/002367 A2 | 1/2007 |
| WO | WO 2007/011549 A1 | 1/2007 |
| WO | WO 2008/002765 A2 | 1/2008 |

OTHER PUBLICATIONS

International Search Report and Written Opinion dated Feb. 22, 2008 for related foreign case PCT/US2007/003570.

International Preliminary Report on Patentability dated Aug. 28, 2008 for related foreign case PCT/US2007/003570.

International Search Report and Written Opinion dated Mar. 17, 2008 for related foreign case PCT/US2007/003804.

International Preliminary Report on Patentability dated Aug. 28, 2008 for related foreign case PCT/US2007/003804.

Office Action dated Jan. 8, 2010 for related Republic of China case 200780013250.7.

Office Action dated Jun. 24, 2010 for related Republic of China case 200780013250.7.

* cited by examiner

METHODS AND SYSTEMS FOR
SIMULTANEOUS REAL-TIME MONITORING
OF OPTICAL SIGNALS FROM MULTIPLE
SOURCES

CROSS-REFERENCE TO RELATED APPLICATIONS

This application claims priority to Provisional U.S. Patent Application No. 60/772,908, filed Feb. 13, 2006, and is a continuation-in-part of U.S. patent application Ser. No. 11/483,413, filed Jul. 7, 2006, the full disclosures of each of which are hereby incorporated herein by reference in their entirety for all purposes.

STATEMENT REGARDING FEDERALLY SPONSORED RESEARCH

Portions of this invention were made under NHGRI Grant No. R01 HG003710-01, and the government may have rights to such inventions.

BACKGROUND OF THE INVENTION

Optical detection systems are generally employed in a wide variety of different analytical operations. For example, simple multi-well plate readers have been ubiquitously employed in analyzing optical signals from fluid based reactions that were being carried out in the various wells of a multiwell plate. These readers generally monitor the fluorescence, luminescence or chromogenic response of the reaction solution that results from a given reaction in each of 96, 384 or 1536 different wells of the multiwell plate.

Other optical detection systems have been developed and widely used in the analysis of analytes in other configurations, such as in flowing systems, i.e., in the capillary electrophoretic separation of molecular species. Typically, these systems have included a fluorescence detection system that directs an excitation light source, e.g., a laser or laser diode, at the capillary, and is capable of detecting when a fluorescent or fluorescently labeled analyte flows past the detection region (see, e.g., ABI 3700 Sequencing systems, Agilent 2100 Bio-Analyzer and ALP systems, etc.)

Still other detection systems direct a scanning laser at surface bound analytes to determine where, on the surface, the analytes have bound. Such systems are widely used in molecular array based systems, where the positional binding of a given fluorescently labeled molecule on an array indicates a characteristic of that molecule, e.g., complementarity or binding affinity to a given molecule (See, e.g., U.S. Pat. No. 5,578,832).

Notwithstanding the availability of a variety of different types of optical detection systems, the development of real-time, highly multiplexed, single molecule analyses has given rise to a need for detection systems that are capable of detecting large numbers of different events, at relatively high speed, and that are capable of deconvolving potentially complex, multi-wavelength signals. The present invention meets these and a variety of other needs.

BRIEF SUMMARY OF THE INVENTION

The present invention is generally directed to systems and methods for monitoring a number of different optical signals from a number of different and discrete sources of such signals. The methods and systems are particularly useful in monitoring chemical and biochemical reactions of interest from an array of reaction regions on a substrate where such reactions are taking place. Of particular interest are the use of these methods and systems in such analytical operations involving relatively high speed, low level signal generation as is found in single molecule analyses, e.g., in nucleic acid sequencing reactions.

In one aspect, the invention provides methods and systems for monitoring one or more optical signals from a substrate having at least a first signal source disposed thereon. The methods typically comprise imaging the optical signal onto an imaging detector that comprises a plurality of pixels. The signal data from a first set of pixels is then subjected to a first data process, wherein the first set of pixels correspond to at least a portion of the imaged signal. The signal data from a second set of pixels different from the first set of pixels is subjected to a second data process different from the first data process. The output of at least the first data process is then recorded to monitor the optical signal.

Relatedly, the systems of this aspect of the invention comprise a substrate having at least a first source of optical signals disposed thereon, an optical train positioned to receive optical signals from the at least first source of optical signals and image the optical signals onto a imaging detector, an imaging detector comprising a plurality of pixels, the detector positioned to receive the image of the optical signals on a first set of pixels in the plurality of pixels, and a processor programmed to process signal data from the detector to monitor the optical signals. In accordance with this aspect of the invention, at least one of the detector or processor are configured to process signal data from the first set of pixels in a first data process and data from a second set of pixels in the plurality of pixels different from the first set of pixels in a second data process different from the first data process.

In another aspect, the invention again provides methods and systems for monitoring an optical signal from a source of optical signals. The methods of this aspect of the invention comprise imaging the optical signal onto a plurality of pixels on an imaging detector, followed by combining signal data from the plurality of pixels, and processing the combined signal data to monitor the optical signal.

The systems of this aspect typically comprise a substrate having at least a first source of optical signals disposed thereon, an optical train positioned to receive optical signals from the at least first source of optical signals and image the optical signals onto an imaging detector, an imaging detector comprising a first plurality of pixels, the detector positioned to receive the image of the optical signals on a second plurality of a pixels in the first plurality of pixels, and a processor programmed to process signal data from the detector to monitor the optical signals. Again, in this aspect of the invention, at least one of the imaging detector and processor are configured to combine signal data from the second plurality of pixels to provide combined signal data, and process the combined signal data.

In another aspect of the invention is provided methods and systems for monitoring a plurality of spectrally distinct optical signals from a source of optical signals. The methods of this aspect of the invention typically comprise passing the plurality of optical signals through an optical train that is configured to image each of the plurality of spectrally distinct optical signals onto an imaging detector, wherein an image of each spectrally distinct optical signal has an image shape characteristic of its spectral characteristics. The plurality of optical signals is then imaged onto the imaging detector. Each optical signal is then identified by its characteristic image shape to monitor the plurality of spectrally distinct optical signals.

The systems of this aspect of the invention typically comprise a substrate having at least a first source of optical signals disposed thereon, the source of optical signals including a plurality of spectrally distinct optical signals. Also included is an optical train positioned to receive the plurality of different optical signals from the at least first source of optical signals and differentially image each of the plurality of different optical signals onto an imaging detector such that an image of each of the different optical signals is characteristic of the spectrally distinct optical signal, an imaging detector, and a processor for processing signal data from the imaging detector, wherein the processor is configured to identify the spectrally distinct optical signal by its characteristic image shape on the imaging detector.

In still other aspects, the invention provides methods and systems for processing an optical image on an imaging detector from a source of optical signals. The methods of this aspect of the invention comprise imaging the optical signal onto an array of pixels on an imaging detector. Signal data is then acquired from the plurality of pixels upon which the optical signal is imaged. The acquired signal data is then transferred to a storage region of the detector, and subjected to a gain process during the transferring step to amplify the signal data.

The systems of this aspect of the invention typically comprise a substrate having at least a first source of optical signals disposed thereon. Also included are an optical train positioned to receive optical signals from the at least first source of optical signals and image the optical signals onto an imaging detector and an imaging detector. Typically, such imaging detector includes a plurality of optically active pixels in an image acquisition portion of the detector, and a data storage portion of the detector operably coupled to the image acquisition portion to receive signal data from the image acquisition portion in a frame transfer process. The detector is configured to apply a gain voltage to the signal data during the frame transfer process to amplify the signal data transferred to the data storage portion of the detector.

In another aspect, the invention provides methods, detectors and systems useful in monitoring optical signals. The methods of this aspect of the invention comprise imaging the optical signals onto an imaging detector that comprises a plurality of pixels. Signal data from the plurality of pixels that falls within a selected signal amplitude range is then selected, and is subjected to a gain protocol to amplify the selected signal data, while not amplifying signal data that was not selected.

Relatedly, the invention provides an imaging detector for carrying out the foregoing method. The detector typically includes a plurality of optically active pixels in an image acquisition portion of the detector, a data storage portion of the detector operably coupled to the image acquisition portion to receive signal data from the image acquisition portion in a frame transfer process, and a gain register operably coupled to the data storage portion to amplify signal data from the data storage portion. The detector is configured to pass signal data through the gain register that falls within a selected signal amplitude range.

The invention also provides methods and systems for monitoring optical signals where the system comprises a source of optical signals, an optical train positioned to receive the optical signals from the source of optical signals and image the optical signals onto an imaging detector, and an imaging detector positioned to receive imaged optical signals onto a plurality of optically sensitive pixels that are operably coupled to a gain register to amplify signal data from the plurality of pixels. The method typically comprises measuring a gain from the gain register in the absence of an imaged optical signal on the plurality of optical signals.

In yet another aspect, the invention provides methods of monitoring a plurality of spectrally different optical signals from a single signal source. These methods typically comprise collecting the spectrally different optical signals in an optical train. The spectrally different optical signals are then transmitted through the optical train that is configured to differentially image each of the spectrally different optical signals onto an imaging detector. Each spectrally different signal imaged upon the detector is then identified by its image on the imaging detector.

In other aspects, the invention provides methods of monitoring optical signals from a plurality of signal sources on a substrate, that comprise imaging the plurality of signal sources onto an imaging detector that comprises a plurality of pixels, wherein images of the plurality of signal sources are directed substantially onto a first subset of the plurality of pixels, but not substantially on a second subset of the plurality of pixels. The signal data from the first subset of pixels but not from the second subset of pixels are then subjected to further data processing to monitor signals from the plurality of signal sources.

Also provided are methods of monitoring one or more signals from a signal source, comprising: imaging a first optical signal onto a first plurality of pixels on an imaging detector; selecting from the first plurality of pixels a first subset pixels that meet or exceed a signal quality threshold; and processing data from the first subset of pixels to monitor the one or more signals from the signal source.

Other methods of the invention for monitoring one or more optical signals from one or more discrete signal sources, comprise: imaging the one or more signals onto a plurality of pixels on a detector array; selecting a subset of the plurality of pixels; recording data from the subset of the plurality of pixels as indicative of the one or more signals; correlating the data to a signal from the discrete signal source.

In still other methods of the invention, a plurality of optical signals from one or more discrete signal sources are monitored. These methods comprise imaging the plurality of signals onto a detector array, wherein each signal is imaged onto a plurality of pixels on the detector array; and processing data from the plurality of pixels while discarding data from pixels not in the plurality of pixels.

The invention also includes systems that comprise: an array of optical signal sources, each signal source being capable of emitting a plurality of signals having different optical wavelengths; an optical train for collecting the signals from the array of signal sources and differentially imaging each of the plurality of signals having different optical wavelengths onto a detector; and a detector for detecting the signals imaged thereon.

The invention is also directed to systems, that comprise an array of a plurality of optical signal sources, the plurality of optical signal sources having a plurality of spectrally resolvable fluorescent compounds associated therewith. The system also includes a source of excitation radiation, a detector array, and an optical train that is configured to direct excitation radiation from the source of excitation radiation to the array of signal sources, receive emitted fluorescent signals from the array of signal sources, and image the fluorescent signals onto the detector array, wherein the optical train is characterized by a dichroic filter in optical communication with an objective lens, wherein the dichroic filter is reflective of the fluorescent signals and transmissive to the excitation radiation.

In still additional aspects, the invention provides methods for resolvably detecting a plurality of spectrally different optical signals from at least a first signal source, comprising: collecting the plurality of spectrally different optical signals from the signal source; and differentially imaging each of the spectrally different optical signals on a detector array, such that each different signal is resolvably detected.

Relatedly, the invention also provides methods of monitoring an optical signal from a signal source, comprising: imaging the optical signal onto a plurality of pixels of a detector array in a signal image; selecting a subset of the plurality of pixels in the signal image having a higher signal intensity within the signal image than other pixels within the signal image; and measuring the signal in the subset of pixels.

Also provided herein are methods of monitoring signals from a plurality of signal sources, comprising: imaging each of the plurality of signals onto a detector array comprising a plurality of rows and columns of pixels; processing data derived from pixels in rows or columns upon which the plurality of signals is imaged, but not from rows of pixels upon which no signal is imaged.

Other methods of the invention for processing signals imaged onto an EMCCD, comprise: determining whether the signals imaged onto the EMCCD are within a preselected signal amplitude range; and processing only signals that are within the preselected amplitude range through a gain register on the EMCCD.

In still other methods of processing signals imaged onto a CCD that is configured to transfer image data acquired by the detector to a storage region on the CCD in a frame transfer process, an elevated voltage is applied to the frame transfer process to amplify signal data being transferred.

In a further aspect, the invention provides systems for monitoring optical signals from a plurality of sources of optical signals, comprising: an array of discrete sources of optical signals, said discrete sources emitting optical signals having different spectral characteristics; an excitation radiation source; a detector array; an optical train configured to: direct excitation radiation from the source of excitation radiation to the array of discrete sources; receive emitted optical signals from the array of signal sources; and differentially image the optical signals having different spectral characteristics onto a detector array; and a processor configured to record the optical signals imaged onto the detector array and correlate the optical signals with a property of or an event occurring within the sources of optical signals.

DETAILED DESCRIPTION OF THE INVENTION

I. Introduction

Figure 1:
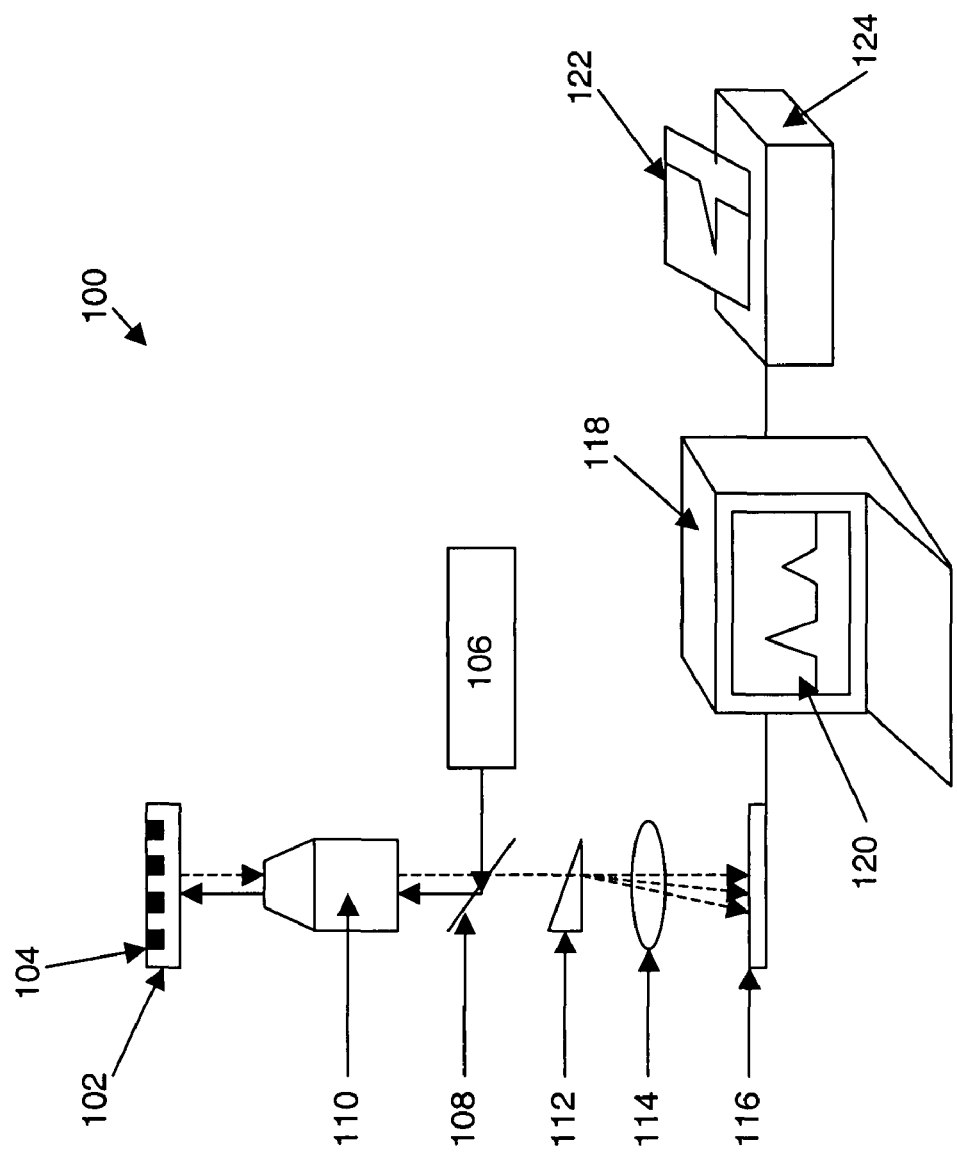
FIG. 1 is a schematic illustration of an overall system the present invention.

The present invention is generally directed to optical detection or monitoring systems, methods enabled by such systems, and components of such systems for monitoring, in real-time, optical signals that emanate from multiple discrete sources of those optical signals. In particular, the optical detection and monitoring systems of the invention are generally capable of monitoring discrete signals from potentially very large numbers of different signal sources, optionally separating and/or deconvolving such signals into constituent signal events, and doing so in real-time, despite that such signals may be changing rapidly, over time.

The systems of the invention thus include all or a portion of a collection of different functional elements. These elements include the multiple discrete sources that include the capability of generating optical signals. In preferred aspects, such sources include chemical, biochemical and/or biological reactants, or mimics of such reactants that are capable of generating optical signals that are indicative of their presence, reaction or conversion. While the sources may be capable of generating optical signals on their own, in preferred cases, a source of excitation radiation is also provided to excite optical signals, e.g., fluorescence, within the sources.

The systems of the invention also typically include optical elements that direct, separate, and/or otherwise alter optical signals from these sources (as well as excitation radiation directed at such sources), in order to ultimately derive optimal amounts of information from such signals when they are ultimately detected. Consequently, the systems of the invention typically include an optical detection system for detecting the potentially large numbers of signals that were directed from the sources, and optionally separated and/or otherwise altered by the optical elements.

Signals detected by the optical detection system are then recorded and processed by appropriate processing systems and data management processes to provide output of the system in user ready formats.

As alluded to previously, the systems of the invention are preferably applied in the monitoring of arrays or collections of spatially discrete chemical, biochemical and/or biological reactions that generate optically detectable signals, such as chromogenic reactions, luminescent or luminogenic reactions, or fluorescent or fluorogenic reactions. A few examples of preferred reactions include those that are regularly performed in the pharmaceutical, biotechnology and healthcare diagnostic fields, i.e., immunoassays, enzymatic assays, receptor assays, nucleic acid hybridization assays, nucleic acid synthesis reactions, cellular assays, and many others.

Typically, the progress of the reactions used in application of the systems described herein result in one or more of the consumption, production and/or conversion of a material that is capable of generating an optically detectable signal, either alone, or in response to an external stimulus, e.g., excitation radiation. By way of example, certain reactants may become fluorescent upon reaction with another reactant, or may have their fluorescence altered or reduced upon such reaction. As such, the fluorescence emitted from the reaction in response to an excitation radiation will change as the reaction progresses. The systems of the invention provide for the source of such signals, e.g., the area in which the reaction occurs, including optionally, the reactants and/or products, the optical elements for collecting, directing and optionally separating and/or altering such signals from such sources, and the ultimate detection of such signals, as well as the manipulation of the resulting data to yield optimal value and information for the user.

The systems of the invention typically include all or a subset of a substrate that includes all or a subset of the sources of optical signals, an optional excitation light source, an optical train that includes the various optical elements for collection, direction and/or manipulation of the optical signals and optional excitation light, optical detectors for receiving, detecting and recording (or putting into a form for recordation) the optical signals, as well as processors for processing data derived from the optical detectors.

A general schematic representation of the system as set forth above, is illustrated in FIG. 1. As shown, the system 100 includes a substrate 102 that includes a plurality of discrete sources of optical signals, e.g., reaction wells or optical confinements 104. An excitation light source, e.g., laser 106, is optionally provided in the system and is positioned to direct excitation radiation at the various signal sources. This is typically done by directing excitation radiation at or through appropriate optical components, e.g., dichroic 108 and objective lens 110, that direct the excitation radiation at the substrate 102, and particularly the signal sources 104. Emitted signals from source 104 are then collected by the optical components, e.g., objective 110, and passed through additional optical elements, e.g., dichroic 108, prism 112 and lens 114, until they are directed to and impinge upon an optical detection system, e.g., detector array 116. The signals are then detected by detector array 116, and the data from that detection is transmitted to an appropriate data processing unit, e.g., computer 118, where the data is subjected to interpretation, analysis, and ultimately presented in a user ready format, e.g., on display 120, or printout 122, from printer 124.

The various functions, applications and components of the systems of the invention are set forth in greater detail below.

II. Substrate

A. Substrate

As alluded to previously, the substrates of the invention, as a general matter, provide the multiple discrete sources of optical signals. In the case of systems for monitoring reactions, such signal sources typically comprise discrete regions in which reactions are taking place and from which discrete optical signals may emanate. In a broad sense, such different regions may comprise reaction wells, or zones that are maintained discrete from other regions by any of a number of different mechanisms, including chemical or physical confinements. Merely by way of example, such regions may comprise discrete patches or zones of immobilized molecules on a surface of the substrate, such as in nucleic acid, protein, antibody or other immuno-arrays, where the reaction being monitored is the association of analytes with such immobilized molecules, they may include channels within a substrate, e.g., microfluidic channel regions, aggregations of capillaries or multiple regions within individual capillaries, or the like.

Alternatively or additionally, such regions may include structural confinements that maintain the reaction components within the discrete regions. Such structural confinements may include wells, depressions, channels, or other structures that retain reaction constituents. Such confinements may also include other barriers that effectively provide structural confinement through, e.g., the use of chemical barriers, e.g., hydrophobic regions surrounding hydrophilic regions on the substrate surface to retain aqueous reaction constituents within the hydrophilic regions.

In still other aspects, such regions may include combinations of the above, e.g., including immobilized reactants within structural confinements. In addition to structural confinements, the reaction regions may comprise optical confinements that may function as or in addition to structural confinements on the substrates, that serve to minimize observation volumes on the substrate through the confinement of excitation illumination and/or the collection of emitted optical signals from relatively small areas or volumes at the reaction region. Such optical confinements may include, e.g., waveguides, such as zero mode waveguides, optical gratings, optical coatings or the like, that can yield the excitation or observation volumes desired on the reaction regions on the substrates.

Typically, the substrates will comprise an optically transparent layer upon which are disposed the reaction regions that provide the discrete sources of optical signals. The optically transparent layer may generally comprise any of a number of transparent solid materials, depending upon other components of the substrate. Such materials include inorganic materials, such as glass, quartz, fused silica, and the like. Alternatively, such materials may include organic materials, such as polymeric substrates such as polystyrene, polypropylene, polyethylene, polymethylmethacrylate (PMMA), and the like, where PMMA is particularly useful in fluorescent or fluorogenic reactions, as it has relatively low autofluorescence.

In preferred aspects, the substrates include zero mode waveguides as the optical confinements to define the discrete reaction regions on the substrate. Zero mode waveguides have been described in, e.g., U.S. Pat. No. 6,917,726, the full disclosure of which is incorporated herein by reference in its entirety for all purposes. Briefly, such waveguides comprise a core disposed through a cladding layer, which in the case of applications to reactions, comprises an aperture disposed through the cladding layer that can receive the reactants to be monitored. Typically, the aperture has at least one cross-sectional dimension, e.g., diameter, which is sufficiently small that light entering the waveguide is prevented in some measure from propagating through the core, effectively resulting in a very small portion of the core and its contents being illuminated, and/or emitting optical signals that exit the core. In the case of optical signals (and excitation radiation), the waveguide cores will typically be between 1 nm and 200 nm, and are preferably between about 10 and 100 nm, and more preferably between about 30 and about 100 nm in diameter.

Optical confinements are typically provided upon the substrate in an array format where a plurality of confinements are provided upon the substrate. In accordance with the invention, arrays of confinements, e.g., zero mode waveguides, are provided in arrays of more than 100, more than 1000, more than 10,000, or even more than 100,000 separate waveguides on a single substrate. In addition, the waveguide arrays typically comprise a relatively high density of waveguides on the surface of the substrate. Such high density typically includes waveguides present at a density of greater than 10 zero mode waveguides per $mm^2$, preferably, greater than 100 waveguides per $mm^2$ of substrate surface area, and more preferably, greater than 500 or even 1000 waveguides per $mm^2$ and in many cases up to or greater than 100,000 waveguides per $mm^2$. Although in many cases, the waveguides in the array are spaced in a regular pattern, e.g., in 2, 5, 10, 25, 50 or 100 or more rows and/or columns of regularly spaced waveguides in a given array, in certain preferred cases, there are advantages to providing the organization of waveguides in an array deviating from a standard row and/or column format.

Optical systems often include a number of optical aberrations, including, e.g., astigmatism, chromatic aberrations, coma, distortion, field curvature, and spherical aberration. In many instances, these optical aberrations become more pronounced as a function off distance from the axial center of the optical imaging system, such that the magnitude of the aberration varies as a function of field position. Accordingly, the optical image is typically most free of aberrations at or near the center of the object field, and is more distorted at the periphery of the object field and system pupil. Because of such aberrations, resolution and accurate monitoring of arrays of discrete nanometer or micron scale sources of optical signals that are provided in a relatively high density becomes increasingly problematic away from the center of the object field. Consequently, performing analyses in a highly multiplexed array of waveguides or other signal sources becomes more difficult.

In accordance with one aspect of the invention, therefore, the sources of discrete optical signals, e.g., the optical confinements, i.e., zero mode waveguides, in array formats, are arranged within the array in a non-regular format, to account to minimize the impact of these expected optical aberrations, and as a result permit more effective multiplexed analyses. In particular, individual sources of signal in the array may be positioned to account for reduced resolution, e.g., between neighboring sources, as a function of distance from the center of the object image. Additionally, or alternatively, the discrete sources may be dimensioned to account for reduced resolution and accuracy at the periphery of the object field. The variance in optical resolution, or conversely, aberration, as a function of distance from the center of the object field are particularly noteworthy in systems that rely upon imaging based detection systems, e.g., that effectively image an entire array or region of an array, that includes multiple different signal sources. Examples of such systems include detector arrays, such as diode arrays, CCDs, i.e., ICCDs and EMC-CDs, and/or CMOS based image sensors, where signals are detected at individual or small groups of pixels on the detector. For example, in CCD based detectors, as signals become more distorted away from the axial center of the imaging system, it becomes increasingly difficult to assign pixel areas on the CCD that correspond to a given signal source in the array of signal sources.

Figure 2:
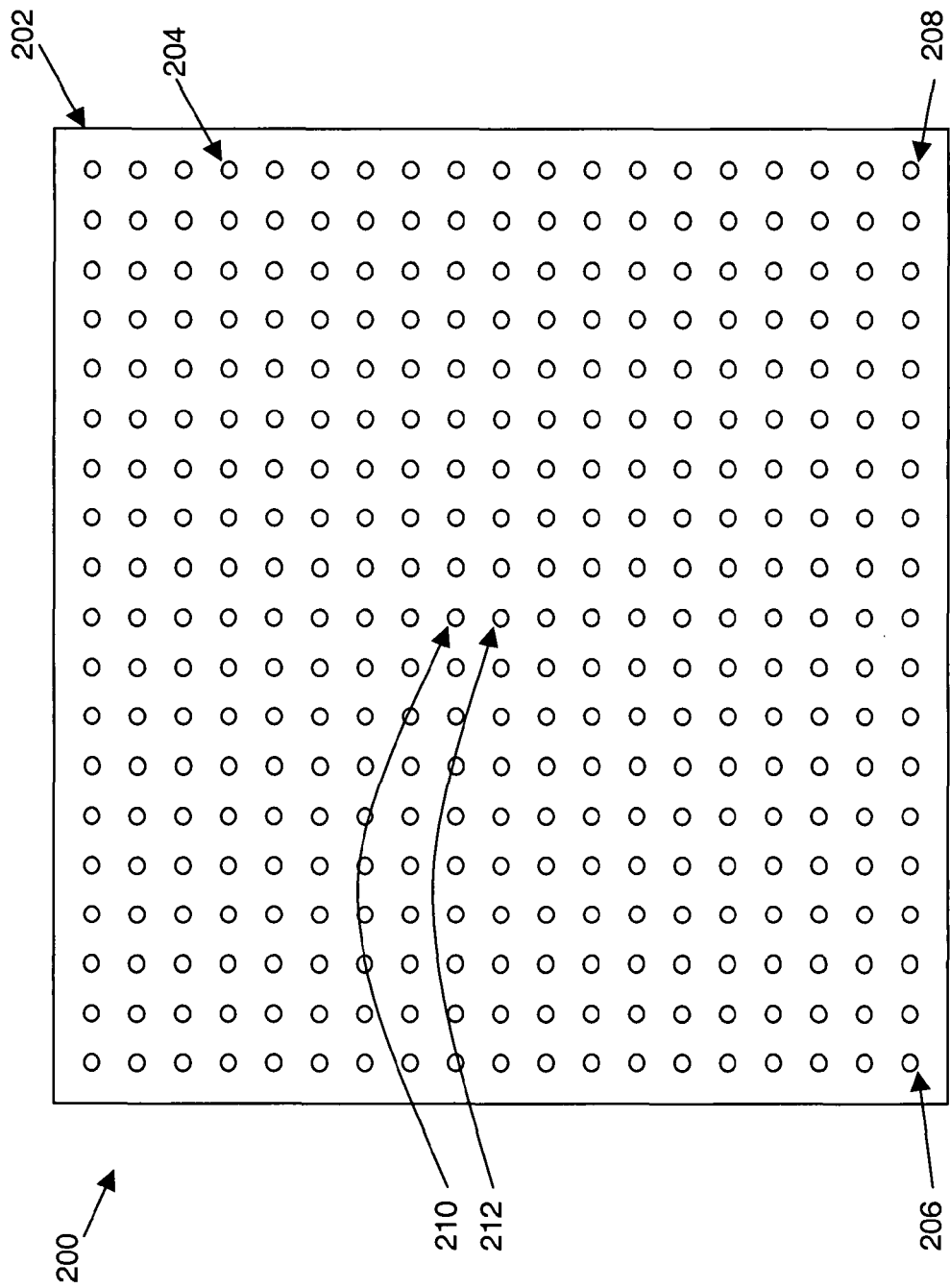
FIG. 2 provides a schematic illustration of an array of signal sources on a substrate, such as zero mode waveguides.
Figure 3:
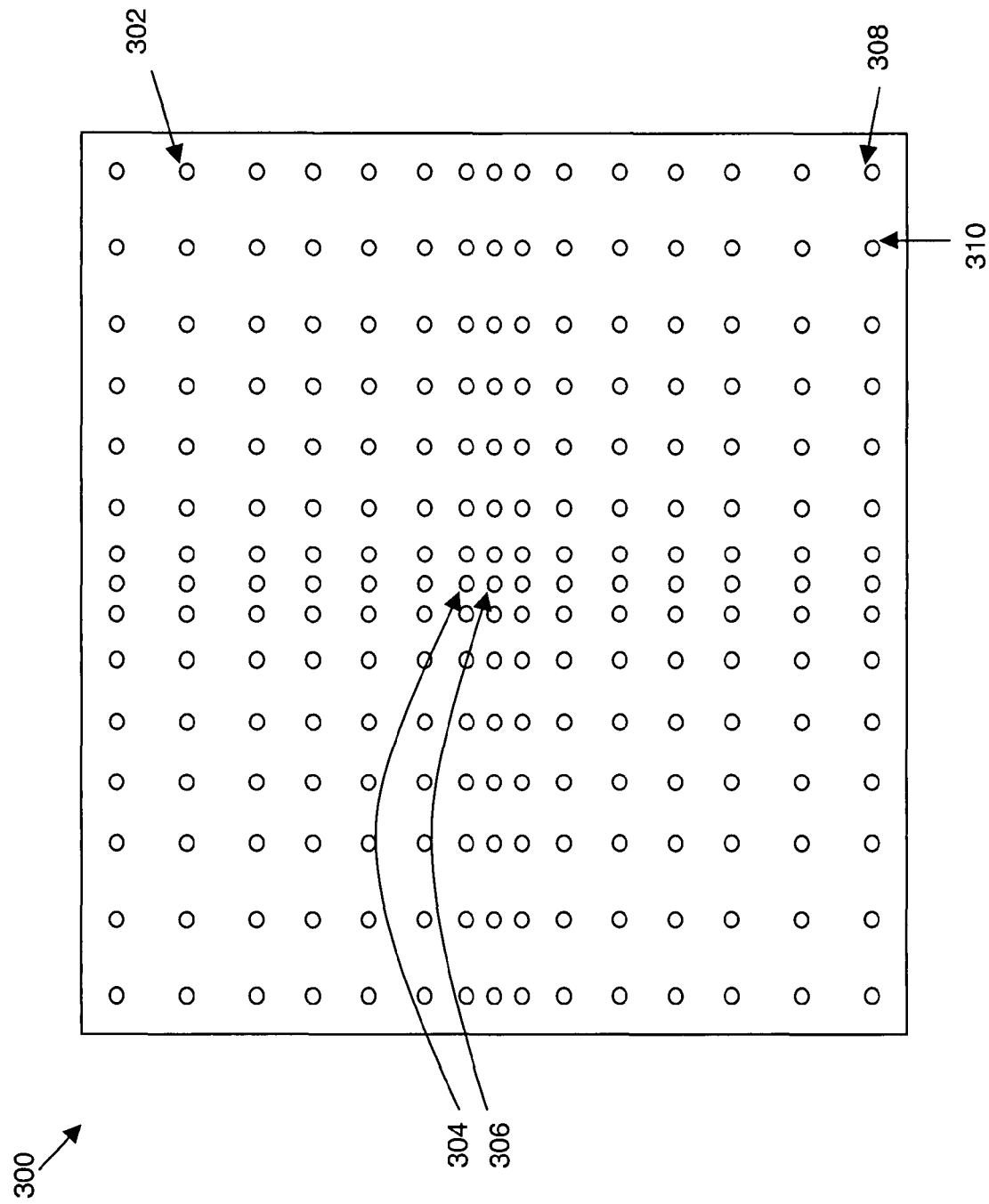
FIG. 3 provides a schematic illustration of an alternative spacing and/or orientation scheme for an array of signal sources, in accordance with certain aspects of the invention.

FIGS. 2 and 3 show a comparative illustration of arrays of sources of optical signals. FIG. 2 shows an array 200 of sources of optical signals (shown as an array of zero mode waveguides 204 in a substrate 202) that includes regularly spaced and consistently sized sources of optical signals. As noted previously, in some cases the sources at the periphery of the array, e.g., sources 206 and 208 would be less resolved, optically, than, e.g., sources 210 and 212. In some cases, it may be the case that aberrations could be sufficient to prevent resolution of the peripheral sources, e.g., 206 and 208. Accordingly, as shown in FIG. 3, an array 300 of sources 302 is provided where the spacing between adjacent sources is increased as a function of the distance from the center of the object image. For example, as shown, signal sources that are nearer the center of the object field represented by the array 300, e.g., sources 304 and 306 are closer together in at least one dimension, than are sources that further away from the center of the object field, e.g., sources 308 and 310, which are more widely spaced in at least one dimension than the more central signal sources. Thus, the space, in at least one dimension between two sources at a first distance from the center of the object field of the optical system will be less than the space, again in at least one dimension, between two sources that are at a second, greater distance from the center of the object field. The spacing between adjacent signal sources may be varied in only one dimension, e.g., varied from left to right, but not from top to bottom, or it may be varied in both dimensions. In the case where the spacing is varied in both dimensions, it will be appreciated that the distance between any two signal sources at the center of the object field, e.g., is less than the space between any two signal sources further away from the center, i.e., on the periphery, of the object field. The foregoing permits greater effective multiplex analysis of arrays of signal sources, such as ZMWs.

Additional arrangements of array elements can be specifically tailored to fit a particular aberration of particular optical systems. For example, if a dominant optical aberration forms a resulting image spot size or shape that is dependant upon field location, then that size or shape can be accommodated in the design of the array of sources by, e.g., appropriately spacing the sources to avoid overlap in image of adjacent sources, or the like. Similarly, if the shape of an imaged source is distorted in one dimension so as to potentially overlap with images of neighboring sources, that source can be dimensioned to reduce that dimension and avoid the overlap, e.g., providing elliptical or rectangular sources.

In a simpler aspect, the signal sources may also be spaced to account for optical manipulations of the signals emanating therefrom. For example, as discussed in greater detail below, in some cases, optical signals are spatially separated into component elements, e.g., light of different wavelength ranges, indicative of different signaling elements, i.e., fluorescent reagents having differing emission spectra. In such cases, it may be desirable to provide sufficient spacing between adjacent signal sources on the substrate to prevent overlap of the spatially separated signals derived from those sources, when those separated signals are incident upon the detector, as set forth below. In this case, increased spacing may only be required in one dimension, e.g., providing sufficient spacing between rows of signal sources, but not necessarily between the columns of signal sources in the array. Alternatively, such additional spacing may be provided in two dimensions. In the case of arrays of signal sources where the signals are subjected to spatial separation before detection, such spacing between adjacent signal sources may generally range from about 0.1 µm to about 10 µm or more, and is preferably from about 0.8 µm to about 3 µm or more.

B. Substrate Interface

The substrates of the invention are typically interfaced with the overall system through an appropriate mounting stage that secures the substrate, provides translational capability to the substrate, e.g., relative to the optical system, and optionally provides additional functionalities, e.g., fluidic interfaces, thermal regulation, e.g., heating or cooling, positional registration, and the like. The mounting stage will also typically include a positioning element that ensures proper positioning and/or orientation of a substrate upon the stage, for subsequent analysis. Such positioning systems may keyed structures on the substrate that are complementary to a corresponding structure on the mounting stage. These may include simple structures, e.g., tooth/notch structures, truncated corner structures, or other distinctive and complementary structures. Alternatively, the keying elements may include electronic keys, such as metal contacts and associated electronic components on the substrate and mounting stage, that indicate when a substrate is positioned properly and in the correct orientation for subsequent analysis. Such key elements may be provided encoded for each substrate, e.g., through incorporated memory elements on the substrate, or through the position and orientation of electrical contacts, to indicate a specific substrate, e.g., lot number, etc. Such identification systems may provide an ability to ascertain whether a given substrate has been used previously, and to what effect. Typically, the mounting stage includes a well or recessed component configured to receive the substrate or the packaged structure containing the substrate, e.g., a multiwell plate format, as well as a biasing mechanism, e.g., spring, clip or other mechanism, for forcibly retaining the substrate in a fixed position on the stage.

Figure 4:
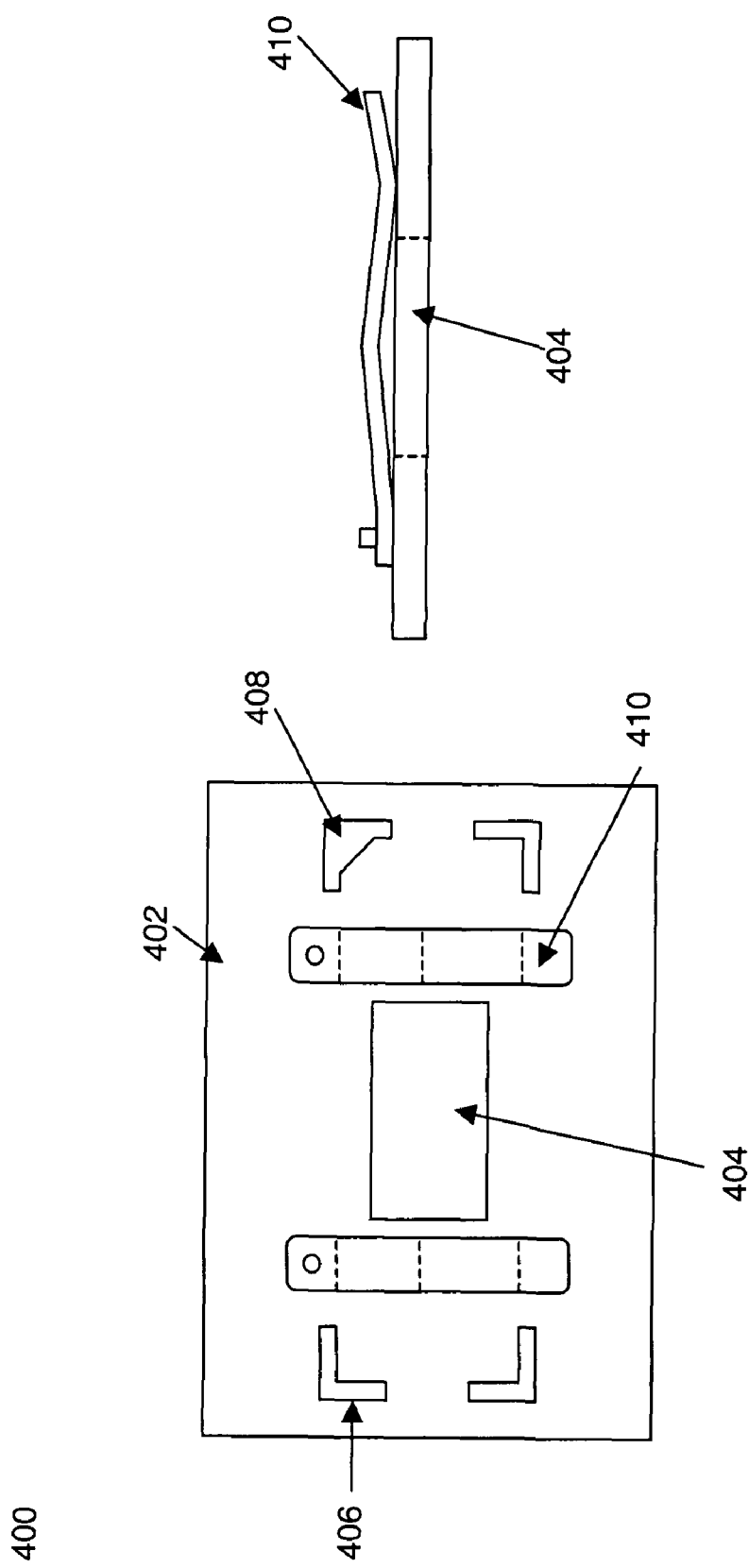
FIG. 4 is a schematic illustration of one example of a mounting stage configured to receive and support substrates bearing signal sources for analysis in the systems of the invention.

One example of a mounting stage is shown in FIG. 4. As shown, the mounting stage 400 includes a platform 402 having a mounting region 404 that receives the substrate (not shown). The mounting region is typically disposed over an aperture 406 in the platform 402 that allows observation of the substrate from underneath. Also as shown, the mounting stage includes structures that facilitate the positioning and alignment of the substrate on the platform. These may include, e.g., ridges 406, recesses or wells, for positioning the substrate, and alignment structures 408, such as pins, bevel structures, tabs, or the like, that correspond to a complementary structure on the substrate, e.g., holes or notches. As noted above, securing mechanisms may also be provided for locking the substrate in place, such as biasing mechanism 410, shown as a clip or a closable cover element, shown also from a side view. Additional components may be provided on the mounting stage, such as a heating or cooling element, additional optical components, and other interfacing elements.

Figure 5:
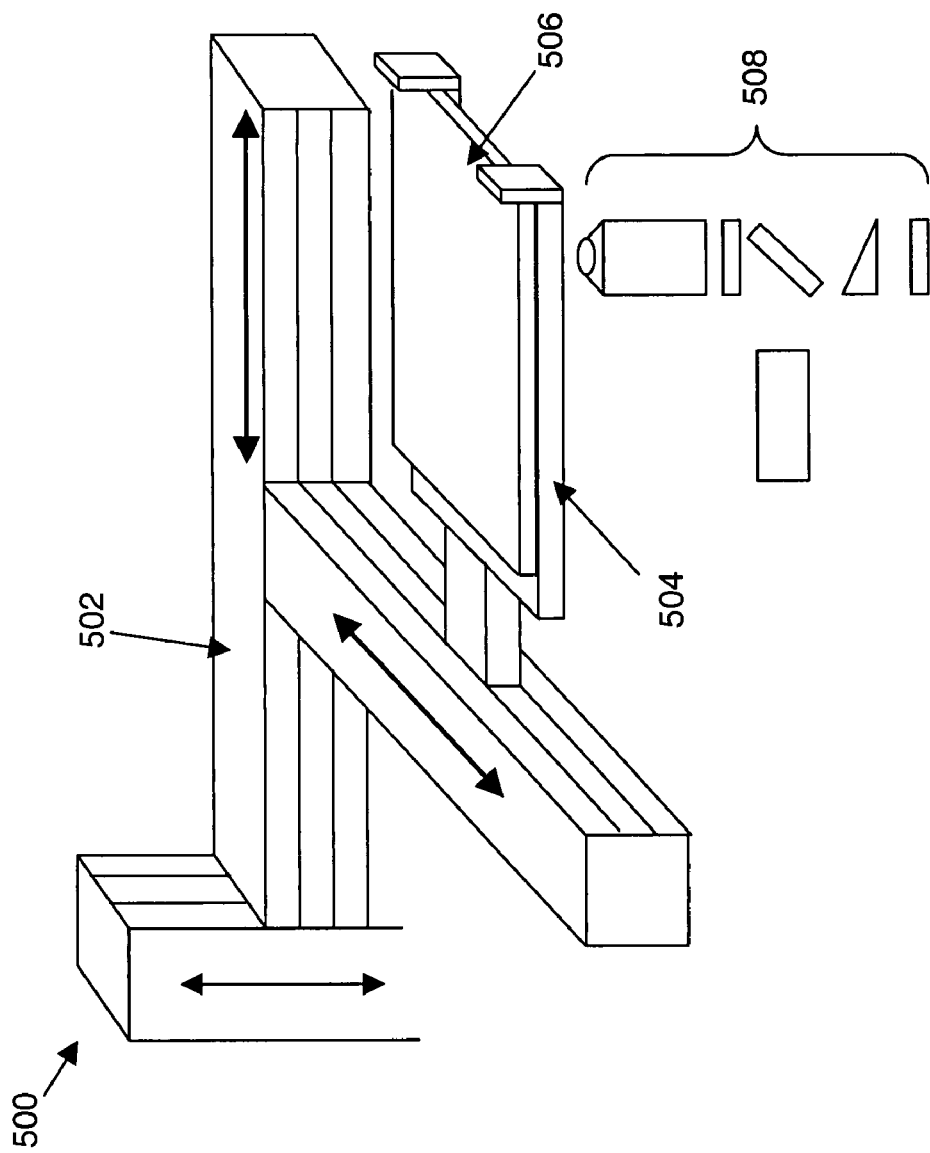
FIG. 5 is a schematic representation of an x-y-z translation robotic system for translating one or more of the substrate and/or the optical train relative to the other, within the systems of the invention.

The mounting stage is also typically coupled to a translation system for moving the stage in two or three dimensions relative to the optical system. The translation system allows scanning of the entire array of signal sources on a substrate, as well as providing an ability to move the substrate toward or away from the optical system for, e.g., focusing, removal of the substrate, addition of components to the substrate, or the like. A variety of x-y-z translation systems are readily available. Additionally, robotic systems are readily available for automating the translation functions of the mounting stage in accordance with preprogrammed instructions. FIG. 5 shows a schematic representation of an entire system 500 including a schematically represented translation system 502 coupled to a mounting stage 504, supporting substrate 506 over optical train 508. As shown, the robotic system includes the capability to move the substrate in any of the x, y, or z dimensions.

Robotic systems may also include components that position substrates upon the mounting stage, apply reagents to the substrates, and the like. A wide variety of such robotic systems that may be applied to the present invention are generally commercially available from, e.g., Tecan, Inc., Caliper Life Sciences, Inc., Beckman, Inc., and the like.

III. Excitation Source

As noted previously, in preferred applications, the systems of the invention are used to monitor luminescent or fluorescent signals emanating form the plurality of discrete signal sources. As such, in many cases, the systems of the invention include a source of excitation radiation. Excitation light sources will generally depend upon the nature of excitation radiation needed for a particular application, e.g., as dictated by the reagents and configuration of a given analysis. For example, the light source may include lamps, e.g., halogen, Mercury, Xenon, or the like, LEDs, lasers, laser diodes, or any other light source capable of directing electromagnetic radiation of a desired excitation wavelength or wavelength range, to the signal sources on the substrate. In preferred aspects, lasers are preferred as the excitation radiation source, due to the coherency and intensity of radiation that they generate in desired excitation wavelength ranges. A variety of different laser types are generally useful for these applications, and include, e.g., ion lasers, solid state direct diode lasers, diode-pumped solid state lasers (DPSS), solid state frequency converted crystal lasers, and the like. In some cases multiple sources may be employed in order to provide multiple different excitation wavelengths. By way of example, in cases where the signal sources include fluorescent compounds, e.g., compounds labeled with fluorescent dyes, multiple different excitation sources may be provided for the various different excitation spectra for such compounds. For example, in the case of compounds labeled with Alexa648 dyes, it will typically be desirable to provide at least an excitation source that provides excitation radiation range that includes light at the 648 nm, the respective excitation wavelengths for these dyes, or if not provided at the nominal peak of the dye absorption curve, the lasers will include sufficient absorption efficiency for the dyes used, such as for Alexa546, where the peak absorption efficiency is closer to 561 nm. In the cases of multiple different dyes, different lasers, e.g., having different wavelength ranges may be used.

IV. Optical Train

As noted previously, the overall systems of the invention typically include an optical train for the direction of excitation radiation to the substrate and the plurality of signal sources thereon, and/or for directing emitted signals from these sources to a detection system that quantifies and records the signal from each signal source. The optical trains used in the overall systems described herein typically include a number of different optical components for use in focusing, directing, splitting, separating, polarizing, and/or collimating the excitation radiation and/or the signals emanating from the discrete sources of signals.

Figure 6:
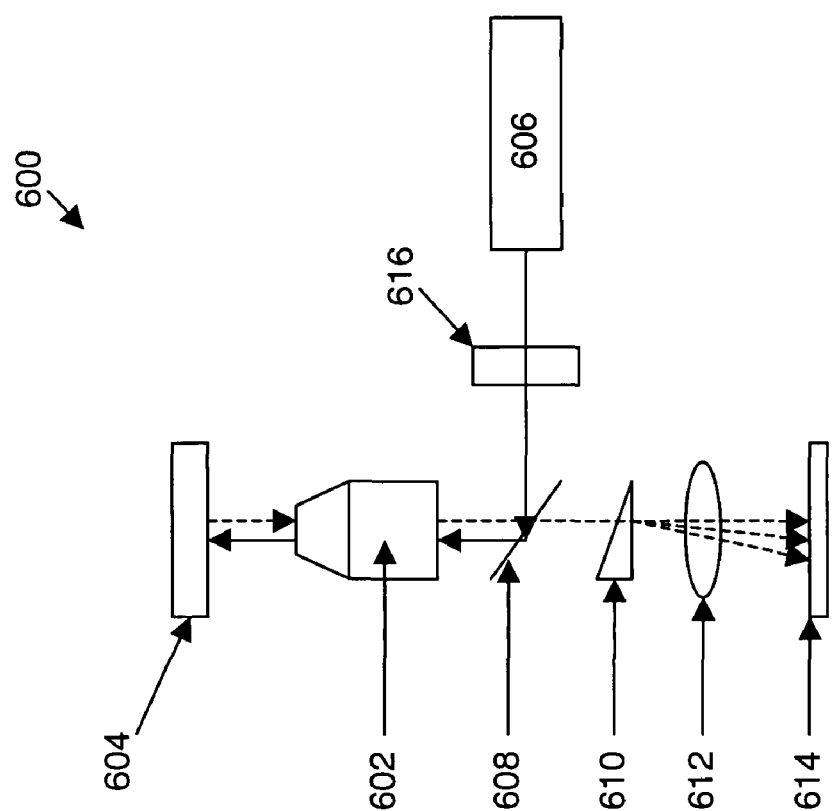
FIG. 6 schematically illustrates the substrate and optical train of the systems of the invention that includes optical componentry for the separation and detection of spectrally resolvable signal components.

A schematic illustration of one optical train is shown in FIG. 6. As shown, the optical train includes an objective lens 602 that is proximal to the substrate 604, and which focuses excitation radiation, e.g., from laser 606, upon a desired location of the substrate, and collects emitted optical signals from the substrate. The optical train will also typically include one or more dichroic mirrors/filters 608, that selectively reflect or pass excitation light and emitted optical signals, to effectively separate signal radiation from reflected or otherwise errant excitation radiation.

The optical train may also optionally include signal separation optics, e.g., to separate optical signals of different wavelengths or direct them to different locations on a detection system. For example, the optical train may include prism 610 that receives the optical signs as from the signal sources, that may include signals of several different primary wavelengths. Alternatively, sets of dichroic filters may be used in a cascading arrangement, to selectively direct each different spectral signal component to a different detector or detector region.

In the case of a prism as a separation element, upon passing through the prism 610, the different wavelength signals are diffracted to different degrees, and as a result, are directed, optionally through additional optical components, i.e., imaging lens 612, at different angles toward the detection system, e.g., detector array 614 allowing for their separate detection and quantitation.

The ability to separate such signals is of particular value in monitoring signal sources that include multiple different reagents that each have a different fluorescent emission spectrum, indicative of a different specific reagent, reaction and/or interaction. A variety of other optical components may be employed in spectrally separating the optical signals, including cutoff filter sets, dichroics, optical gratings, and the like. Such components will typically be arranged to direct different portions of each optical signal to different detectors or, preferably, different locations upon the same detector or array of detectors. In accordance with the invention, different signals may be spectrally resolved by differentially imaging such signal components onto the detector, e.g., detector array 614. Such differential imaging may be entirely spatially distinct, e.g., by being directed to different detectors or locations on the same detector, or they may conformationally distinct, e.g., providing an imaged signal that is of a different shape than an image of a different signal component, such that it can be resolved. For ease of discussion, both shall be generally referred to herein as being spatially resolved or separated or directed to different or regions of the detector, although in some cases, such different regions will be understood to overlap.

Other components that separate portions of the optical signals are also optionally included in the optical train, depending upon the application to which the system is to be put, including spatial filters, e.g., to confine the optical signals that are directed to the detector, polarizing filters, to pass signals that are in one polar optical plane, or the like. For example, in addition to separation of signals of differing wavelengths, the optical train may also include splitters, e.g., beam splitters, optical gratings, lens or microlens arrays, and the like, that serve to divide up the excitation radiation and/or the emitted signals to direct it to different locations, or other optical components that change the spatial configuration of excitation radiation, e.g., optional optical grating 616. In some cases, additional filters may be added after the laser to filter the main laser line by removing or reducing any optical noise that may be inherent in the laser, as well as in front of the detectors to reduce or remove any unwanted stray light that may be generated or reflected from the system as a whole, or the ambient light.

In particular, in certain aspects, one or more of the optical train and/or the excitation radiation source may be configured so as to provide excitation illumination of a large number of discrete signal sources on the substrate simultaneously. In the case of arrays of zero mode waveguides, for example, the optical train and/or the excitation radiation source provide illumination to a large number of zero mode waveguides, simultaneously. As noted below, the optical trains are also typically capable of collecting and detecting signals from the same or similar large numbers of the signal sources, or in this example, zero mode waveguides. The systems typically illuminate at least 2 signal sources, simultaneously, preferably, greater than 10 signal sources simultaneously, and more preferably, greater than 100 signal sources, simultaneously. In some cases, it may be desirable to use the systems described herein, for the excitation of 1000, 10,000 or more discrete signal sources. Systems that split excitation beams or apply multiple excitation sources (both with or without beam splitting) are particularly useful for directing excitation radiation to larger numbers of signal sources.

Simultaneous illumination with excitation radiation over large numbers of signal sources may generally be accomplished through a variety of different means, as noted above. For example, one may focus a relatively large spot size upon a large array of signal sources. However, as will be appreciated, because laser power is limited, and indiscriminate illumination may cause certain adverse effects, e.g., heating, it may be desirable to avoid illuminating non-signal generating portions of the substrate. Additionally, in many cases, the non-signal generating regions of the substrate may provide additional noise through reflection of the laser light. For example, in the case of arrays of zero mode waveguides using a thin film metal cladding layer, spaces between signal generating regions are highly reflective. Such reflected activation radiation gives rise to elevated noise levels for the system.

Figure 8:
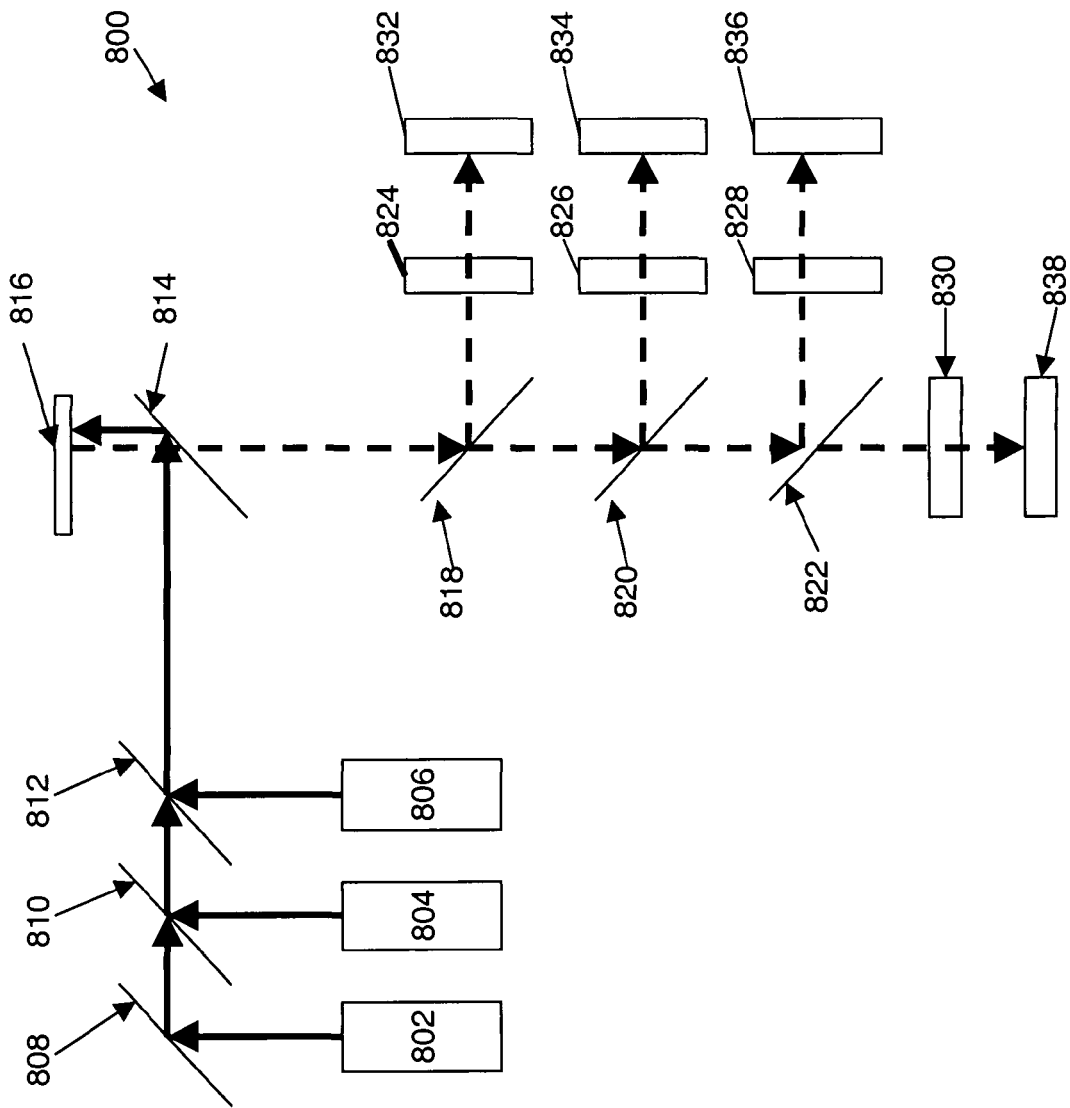
FIG. 8 provides a schematic illustration of a multiple excitation source/multiple emission wavelength system that utilizes transmissive fluorescence optics.
Figure 9:
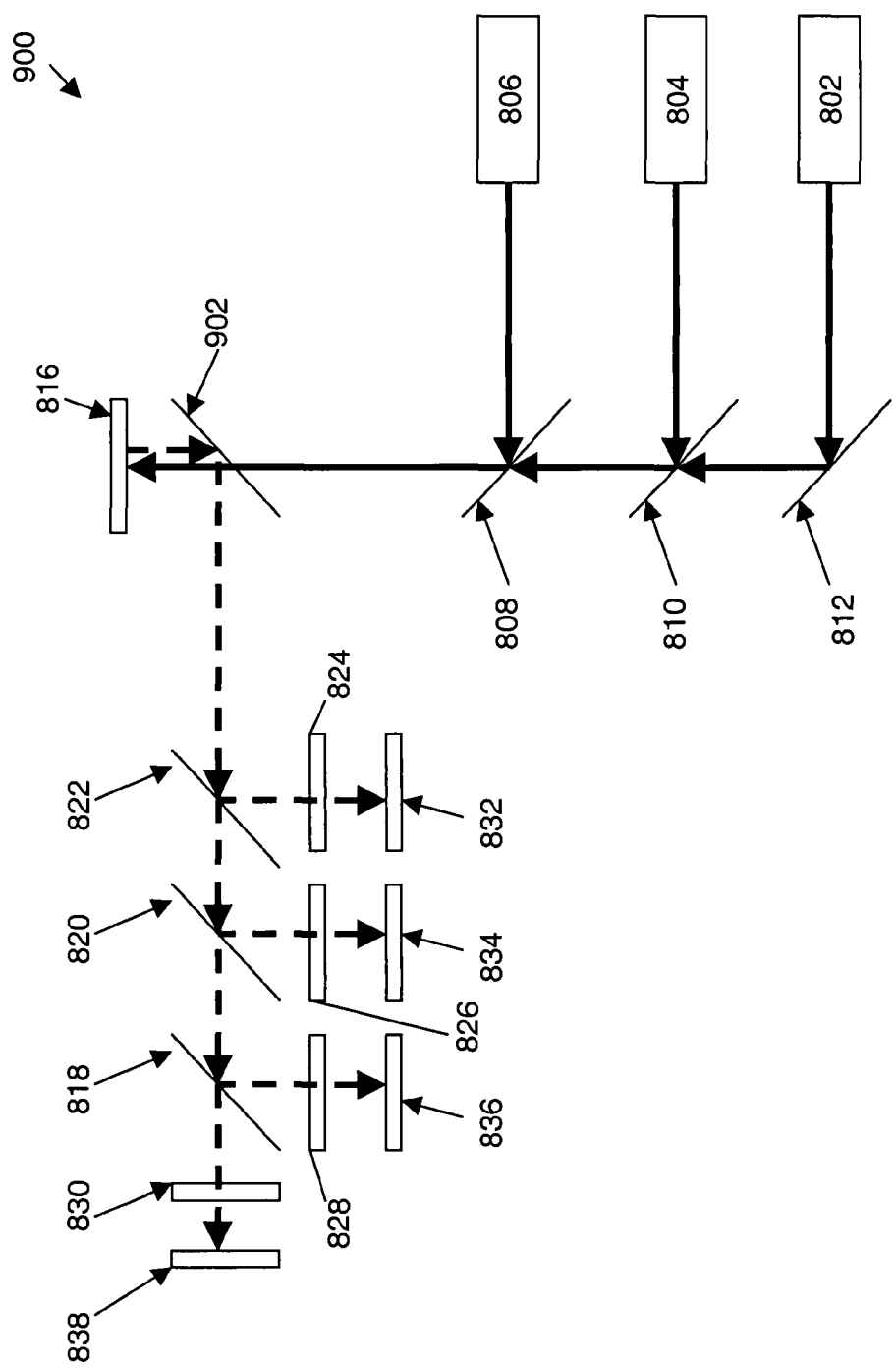
FIG. 9 provides a schematic illustration of a multiple excitation source/multiple emission wavelength system that utilizes reflective fluorescence optics.

In some cases, larger excitation regions may be provided by directing multiple different excitation sources at a given substrate to provide illumination of larger numbers of signal sources, e.g., laser 606 and optional additional lasers, e.g., as shown in FIGS. 8 and 9. Unfortunately, use of multiple different sources may provide issues regarding differences between the individual sources, e.g., wavelength, frequency or intensity of illumination that may impact the signals resulting therefrom, e.g., rendering slightly different signal profiles. Additionally, such multiple excitation source systems may still give rise to the problems of excessive illumination of the substrate, as a whole. Similarly, excitation light beams may be divided into multiple beams, e.g., using beam splitters, optical gratings or other optical components, as alluded to above, to direct multiple discrete excitation illumination spots at different locations of the substrate, and as a result, illuminating larger numbers of signal sources thereon. In a related aspect, lenses may be provided that stretch the beam spot into an elliptical or elongated spot shape.

In certain preferred arrangements, individual or multiple excitation radiation source(s) may be manipulated to provide preferential illumination on the signal sources on a substrate, and reduce or eliminate illumination at regions of the substrate not occupied by the signal source(s). A number of methods may be used to modulate the illumination profile of the excitation light source to preferentially provide excitation illumination at the signal sources on the substrate, and, in particularly preferred aspects, less illumination at the spaces not occupied by such signal sources. In general, this is accomplished by using optical elements that provide a signal profile at the object plane of the optical train, e.g., the substrate, that peaks in intensity at positions in the object plane that correspond to the position of the signal sources on the substrate. A variety of different optical elements may be used to achieve this illumination profile. For example, where illumination at a low frequency is not an issue for analysis of the signal sources, one may simply employ reciprocating beam, e.g., through the use of a galvo-equipped laser system. In cases where low frequency illumination is or can be an issue, one may employ holographic or diffractive optical elements to achieve the desired illumination profile, e.g., in rows of lines, grids, or the like.

In particularly preferred aspects, cylindrical lenses or microlenses, or arrays of cylindrical lenses or microlenses are used to modulate the excitation light to provide illumination in a linear format so as to preferentially illuminate regions that include signal sources, and do not illuminate regions of the substrate that include no signal sources. Further, such optical elements may yield excitation illumination profiles on the substrate in multiple lines, i.e., in parallel and/or in orthogonal orientation, e.g., as a grid, or the like. For purposes of discussion, and with reference to direction at the substrate and included arrays of signal sources, the "laser spot" or "excitation radiation spot" refers to any of a variety of different beam shapes, configurations and orientations that are incident upon the substrate, including ellipses, lines, grids, and the like. As will be appreciated, when selectively directing excitation radiation at the signal sources on the substrate, the system may be equipped with certain alignment tools to facilitate alignment of the excitation radiation with the arrays of signal sources on the substrate. Such tools may include reference positions on the substrate that may be identified, either manually or automatically, by the system, to orient and/or focus the system appropriately on the array of signal sources on the substrate.

Figure 7:
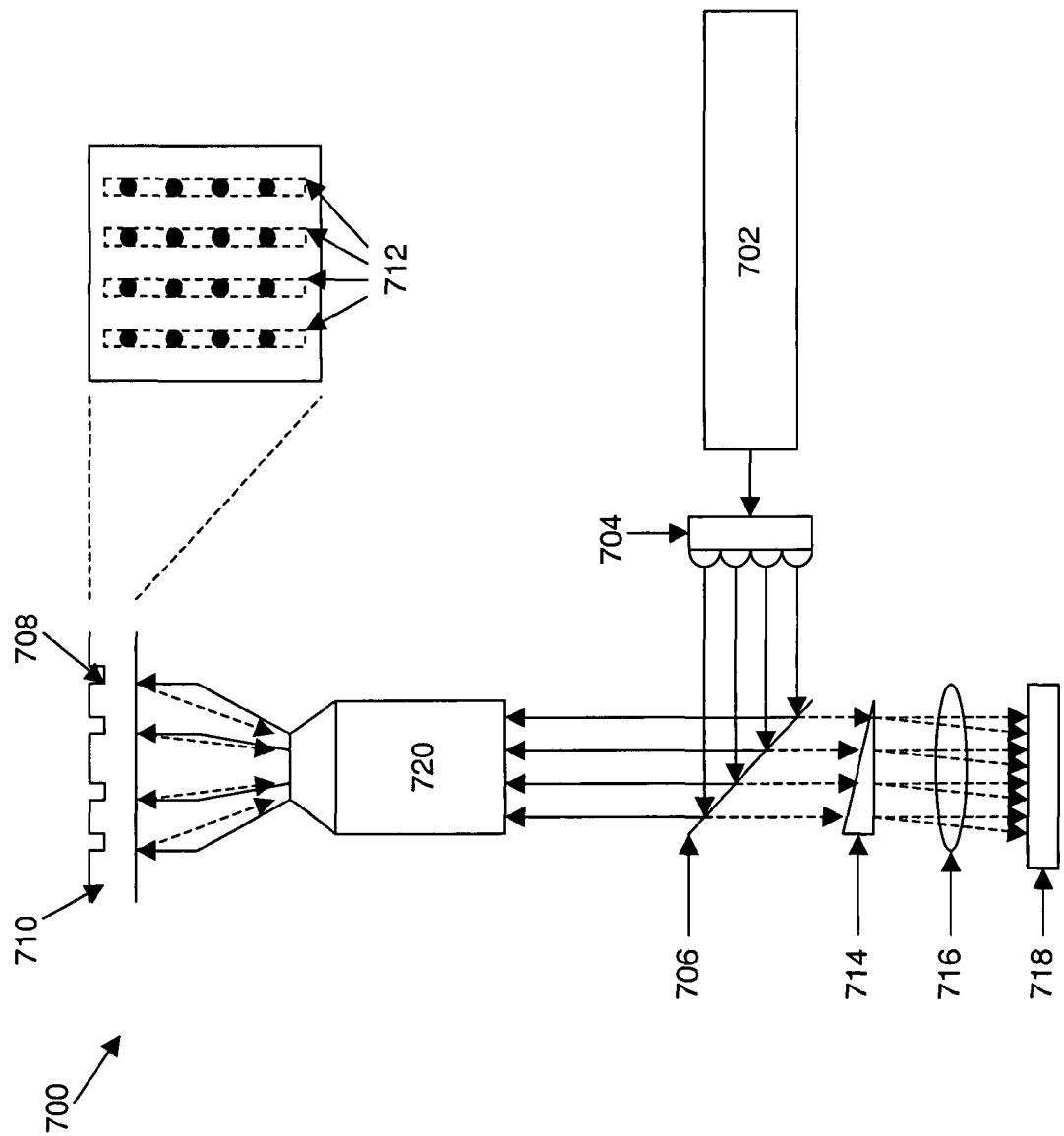
FIG. 7 provides a schematic illustration of a system of the present invention that includes optical componentry for simultaneous illumination of larger numbers of signal sources on the substrates.

A schematic illustration of this aspect of the invention is shown in FIG. 7. As shown, the excitation illumination portion of an overall system 700 includes the excitation light source, e.g., laser 702, that is directed through an appropriate optical element, here shown as an array of cylindrical lenses 704, to an appropriate dichroic mirror, e.g., dichroic 706, which directs the excitation radiation (shown as solid arrows) up through objective lens 720 and toward substrate 710. As noted previously, the spatial profile of the excitation radiation is configured to preferentially provide greater excitation radiation at the various signal sources 708 on the substrate 710, which is in the focal plane of the objective lens 720. An alternate view of substrate 710 shows the illumination profile as a series of parallel illumination regions on the substrate (as indicated by the dashed outlines 712).

As described elsewhere, herein, the emitted fluorescence or other optical signals from the signal sources, are then collected by objective 720, passed through dichroic 706, and are optionally subjected to spectral separation of the signal components, e.g., via prism 714, and ultimately directed to a detector, e.g., detector array 718. In addition to the various optical components already discussed, the optical trains of the systems described herein may also include one or more imaging lenses, e.g., lens 716, to provide a resolved image of the separated, and directed optical signals onto an image plane of, e.g., a detector array 718.

While linear laser or illumination "spots" are preferably aligned to be collinear with rows and/or columns of spatially arrayed signal sources, it will be appreciated that such illumination lines may be provided at an angle that is offset from the linear arrangement of the signal sources, but still illuminating multiple different signal sources simultaneously. In particular, by offsetting the illumination lines by a selected angle, one can still ensure that illumination of multiple regularly arrayed or gridded signal sources are illuminated. In its simplest form, for example, an illumination line rotated at 45° from the linear arrangement of signal sources in a grid will still illuminate those signal sources that lie on the diagonal. Similarly, as with regularly spaced rows of crops passed by on the adjoining roads, numerous specific angles provide linear arrangements of adjacent signal sources. As will be appreciated, the angles that provide effective illumination across multiple different signal sources in a gridded array format will generally depend upon the spacing of the sources in each dimension. For regularly spaced sources, e.g., equally spaced in two dimensions, for example, lines at 0°, 22.5°, 45°, 67.5° and 90° angles from the row or column orientation of the gridded array of signal sources will generally run parallel to lines that include multiple sources. A number of angles between these will likewise provide illumination of multiple sources.

The various components of the optical train, e.g., lenses, gratings, filters, prisms, beam splitters, and the like, are generally obtainable commercially from optics suppliers, including, for example, Special Optics, Inc., Newport Corporation, Thorlabs, Inc., CVI Lasers, Lambda Research Optics, Lambda Physics, and Precision Optical, Inc.

In some aspects, the optical train for use in the systems of the present invention utilizes a configuration based upon reflective fluorescence filters that more readily permit implementation of multi-light source, e.g., laser, excitation systems, that may be useful for multi-fluorophore systems, e.g., signal sources that include multiple different fluorophores in generating the signals.

In conventional fluorescence detection schemes, interference filters are typically employed that reflect excitation light at an angle of approximately 90° such that is incident upon the fluorescent sample, and transmit fluorescent light emitted from that sample such that its wave-front remains relatively undisturbed. While the degree of rejected excitation light attainable in such transmissive fluorescence geometries is sufficient for most one or two excitation band applications, these current schemes may not be effectively extended to three or four excitation band schemes, as a single transmissive-fluorescence filter that efficiently passes substantial portions of multiple, e.g., 2, 3, 4 or more, different fluorescent spectra while reflecting the multiple excitation bands, is not readily manufacturable using available technology. Further, while multiple filter components could be combined to achieve this in a multiple laser, multiple emission wavelength system, increased transmission losses, increased optical aberrations, increased size, and increased costs for making higher performance fluorescence transmissive filter systems, make such solutions less desirable.

In contrast, the optical trains of certain preferred configurations of the systems of the invention utilize a reflective fluorescence filter setup in selectively directing emitted light to the detector while blocking excitation light that is reflected from the substrate or other components in the system. In particular, the optical trains of this aspect of the invention typically include at least one optical filter component that reflects emitted fluorescent light from the substrate to direct it to a detector, rather than passing such light. The systems of the invention include a multi-band reflective dichroic filter that selectively reflects multiple emitted fluorescent wavelength ranges, e.g., emitted by multiple different fluorescent materials having distinct emission spectra. In addition to their multi-band reflectivity, these filter components are typically capable of passing excitation light (light at the desired excitation wavelength). As such, the multi-band dichroic are tailored to transmit excitation radiation at multiple different wavelengths, while generally reflecting the longer wavelength emitted fluorescence. The dichroics are further tailored to include relatively narrow reflective ranges, so as to permit transmission of excitation bands that fall between or among two or more emission bands. Such reflective fluorescence systems benefit from superior performance dichroics, as compared to the transmissive dichroics, and also have cost and simplicity benefits.

Because the narrow-band selectivity is applied in reflection versus transmission, more of the reflected excitation radiation is filtered by being transmitted through the multi-band dichroic, and not reflected. To the extent that any excitation radiation is reflected by the multiband dichroic, it can be selectively filtered out following separation of the individual excitation spectra (also referred to as 'color separation'), using an individual narrow-band notch filter that is applied to one separated color (e.g., one selected emission spectrum), as all colors or emission spectra. As a result, any transmission losses are only applied to an individual spectrum, and not over the entire emission spectra. Further, fabrication of a single multi-narrow band reflective filter is more readily achievable using available technology than a narrow multi-band transmissive filter.

FIGS. 8 and 9 provide schematic illustrations of conventional fluorescence transmissive optical trains and the fluorescence reflective optical trains of the invention. For ease of discussion, components that are common among the two configurations are given the same reference numbers. As shown in FIG. 8, a fluorescence transmissive optical train 800 includes at least a first excitation light source, e.g., laser 806. For multi-band excitation, one or more additional light sources, e.g., lasers 802 and 804 are optionally included. Where such additional light sources are included, they are typically coupled with and directed at dichroic filters, e.g., dichroics 808, 810 and 812, respectively, so that all of the excitation radiation from the various sources is co-directed, as indicated by the solid arrows. The excitation light is then directed at a multiband dichroic filter 814 that reflects substantially all of the excitation radiation at the substrate 816 that is being subjected to analysis. Fluorescent signals emitted from the substrate or sample surface are then passed through the multiband dichroic 814, which is transmissive to light at the wavelengths of the emitted fluorescence, along with some portion of reflected excitation radiation. In the case of multiple different fluorescent emission spectra, the emitted fluorescence is then subjected to a color separation step, where the different individual emission spectra are separated from each other and separately detected. Color separation may be accomplished using a series of cascaded dichroic filters, such as filters 818, 820, and 822 whereby a selected emission spectra is reflected from each of the dichroics onto an adjacent detector 832, 834 and 836, respectively, with the last emission spectrum transmitting through all of the dichroics to be incident onto detector 838). Alternatively, a prism based color separation process may be employed where different emission spectra are directed through an appropriate optical grating or prism to spatially separate the individual spectra and direct them to different detectors or different regions on an array detector. Additional filter elements, e.g., notch filters 824-830 may be included within the optical train to further tailor the emission radiation detected at each of the detectors, e.g., to filter out any inadvertent reflected excitation or emission light. As will be appreciated additional lasers, e.g., fourth fifth, etc. lasers, may be included in the system with the concomitant inclusion of additional optical elements, e.g., filters, dichroics, etc.

In contrast, FIG. 9 provides a schematic illustration of a fluorescence reflective optical train, in accordance with certain aspects of the invention. As shown, although in a different orientation, the system includes similar excitation light sources (e.g., lasers 802-806) and dichroics (808-812) to codirect the excitation radiation. However, in contrast to FIG. 8, the excitation light is directed at and transmitted, rather than reflected by multi-band dichroic 902, which is tailored to be reflective of multiple, narrow bands of emitted fluorescence. The excitation radiation is then transmitted, rather than reflected, by dichroic 902. Emitted fluorescence is then reflected, rather than transmitted by dichroic 902, and then subjected to optional separation and detection, e.g., in a similar manner to that shown in FIG. 8. As will be appreciated, although the dichroics are shown oriented at 45° angles in the system to reflect light, e.g., fluorescence as in FIG. 9, at 90° angles relative to its angle of incidence, in some cases it may be desirable to reflect the light at greater than a 90° angle, e.g., rotating the dichroic so that the angle of incidence of both the transmitted excitation light and emitted fluorescence is shallower than 45°, as such higher reflectance angles provide for simplification in dichroic fabrication.

The optical train included in the systems of the invention also may include an autofocus function for automatically adjusting the objective or other lenses in the optical system to focus the sample material being analyzed within the focal plane of the optical train. A variety of different autofocus systems may generally be incorporated into the systems of the invention.

As noted elsewhere herein, the optical trains of the invention, whether based upon fluorescence transmission or reflectance, typically directs the emitted, and preferably separated, fluorescent signals to a detector. In particularly preferred aspects, the detector comprises an array of point detectors, such as a diode array detector or a charge coupled device (CCD, ICCD or EMCCD). In the case of such array detectors, it may be desirable for the optical train to provide the directed fluorescence onto the detector in a particular desired configuration. For example, in some cases, it is desirable to image a fluorescent signal onto a plurality of pixels that exceeds a minimum threshold level. For example, providing sufficient signal data from at least 2 pixels, preferably at least 4 pixels, and more preferably at least 10, 20 or even 100 pixels may be desirable to provide for enhanced statistical evaluation of data. In accordance with this aspect of the invention, the data from these multiple pixels will typically be combined before or during the processing of the signal data therefrom. In some cases, the signal data from the selected pixels would be averaged and/or subject to correction, e.g., for background signal or noise, in order to provide optimal statistical confidence in a given data. In still other cases, the data may be combined prior to substantive processing, in order to reduce the data load that is subjected to the various processing steps, e.g., in a gain register or other processing system. In particular, and as described in greater detail below, like data, e.g., corresponding to a single signal or to background or quiet pixels, may be co-processed in order to minimize the amount of individual data units that are subject to such processing, and thus reduce the processing requirements of the overall system.

In the case of signals having multiple, separated spectral components, it may be desirable to image each different fluorescent signal component, e.g., each differently colored spot of emitted fluorescence, onto a plurality of pixels of an array detector, so that variations in intensity across an individual signal spot may be accommodated in data analysis, e.g., averaged, discarded, etc. For example, in many cases, each signal component will be imaged on at least two pixels in a detector array, preferably at least 4 or more pixels in the detector array, and in some cases upwards of 10, 20 or 50 or more pixels.

In the case of signal sources, e.g., sample substrates that include an array of discrete signal sources, the total number of pixels involved in detection of a given spectral signal from the overall array will typically vary approximately by the multiple of the sources being analyzed. For example, if each separated color signal from each discrete signal source on an array is imaged onto 4 pixels in the detector array, and 10 signal sources were being analyzed using the same array, then the aggregate signal for that color for the entire array of signal sources would be imaged onto approximately 40 pixels of the detector array. As has been reiterated herein, in particularly preferred aspects, the imaged signal will typically include at least two separated spectral components, and preferably 3, 4 or more spectral components that are directed to and imaged upon different detectors or regions on a detector array, utilizing a range of numbers of pixels.

V. Detector

The systems of the invention may generally include any of a variety of different detector types useful for detecting optical signals that are directed to the detector. Examples of different types of detectors include photodiodes, avalanche photodiodes, photomultiplier tubes, imaging detectors, such as charge coupled devices, CMOS (complementary metal oxide semiconductor) sensors or imagers, CCD/CMOS hybrid imagers, and the like. In preferred aspects, imaging detectors are employed in the systems of the invention, so as to provide simultaneous detection over larger areas of the substrates, and consequently, larger numbers of discrete signal sources. Charge coupled device based detectors (CCDs) and CMOS image sensors are particularly preferred for their ability to simultaneously detect and/or monitor signals from large numbers of discrete signal sources on the substrate. Because data derived from these types of image or imaging detectors is assigned to discrete pixels, signals from discrete sources that are incident upon different locations of the detector may be separately detected and quantified. Further, in applications where relatively high speed, and relatively low signal levels are prevalent, e.g., where the signal sources comprise single molecule type reactions, highly sensitive detectors are generally preferred, such as electron multiplying CCDs (EMCCD) or intensified CCDs (ICCD). Typically, EMCCDs are preferred for their sensitivity to low signal levels.

Figure 10:
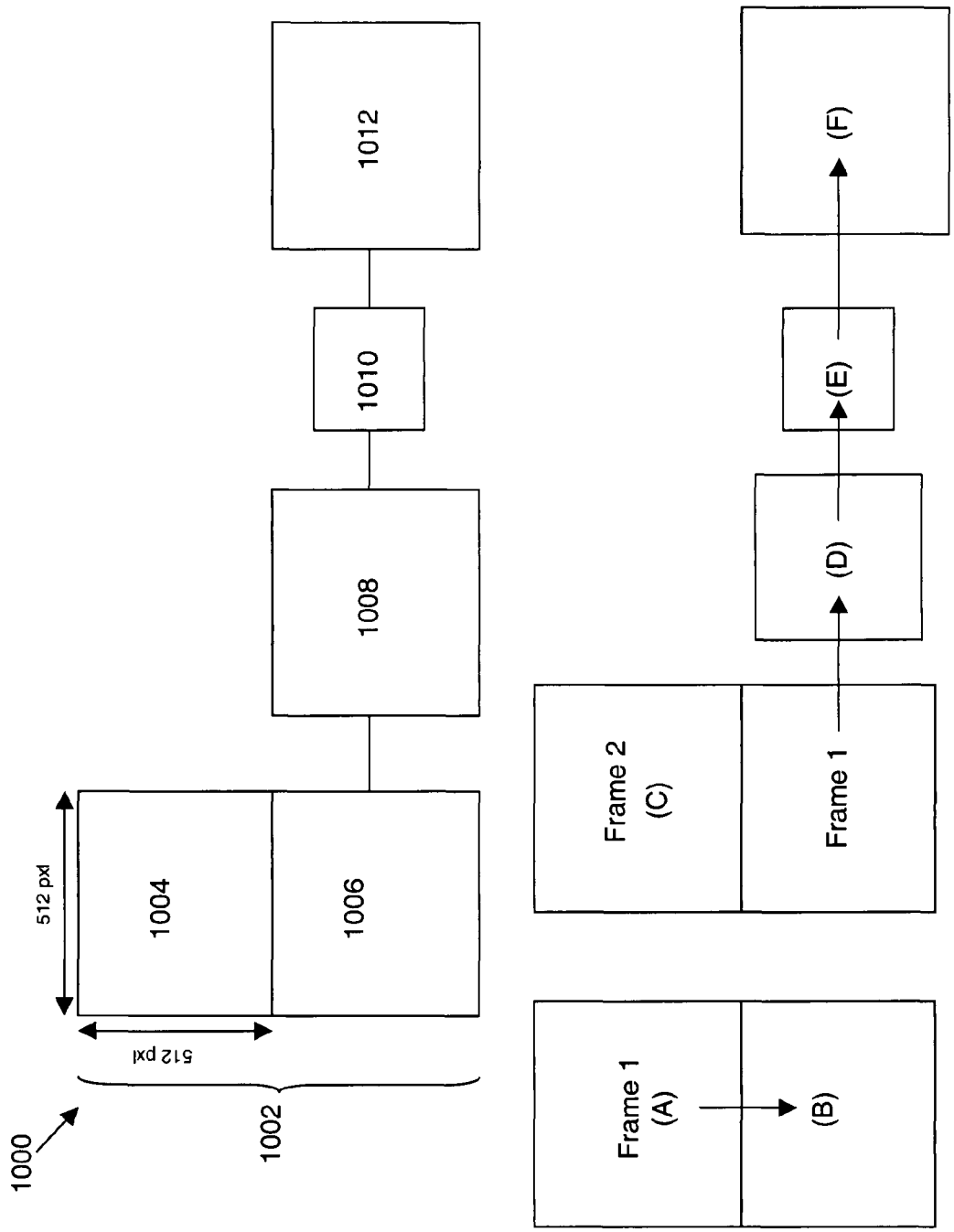
FIG. 10 provides a block diagram illustrating the operation of an EMCCD detector and data processing steps of certain aspect s of the invention.

FIG. 10 provides a schematic illustration of the operation of an exemplary EMCCD in processing image data. As shown, an overall system 1000 includes a typical EMCCD chip 1002, which has an image area 1004 and a storage area 1006. The CCD includes an EM gain register 1008 that is operably connected to an appropriate analog:digital converter 1010, which is, in turn, connected to a processor or computer, e.g., computer 1012. As shown, each area comprises a 512× 512 pixel array. As shown in step A, an image is acquired (Step A) (Frame 1) in the image area 1004 and transferred to the storage area 1006 (step B) so that the image area is available for acquiring subsequent images, e.g., Frame 2 (Step C). In the case of some EMCCDs, the frame transfer requires an applied potential of approximately 2V. The frame in the storage area (Frame 1, as shown) is then transferred into the EM Gain register 1008 pipeline (step D) (again, requiring approximately 2V), where the charge associated with the image is passed through approximately 536 stages to achieve a potential gain range, that is software controllable, from 1 to of 2000×. The EM gain register processing typically requires approximately 50V. The amplified image data is then passed through an analog to digital converter 1010 (step E) to be stored or further processed by a computer 1012 (step F).

As with the illumination of signal sources, in preferred aspects, the detection systems in the systems of the invention are typically capable of detecting and/or monitoring signals from at least 2 different signal sources, simultaneously, preferably, at least 10 discrete signal sources, and in many cases, more than 100 or even more than 1000 discrete signal sources, simultaneously. Further, the detectors are likewise capable of monitoring or detecting multiple, spatially separated signals or signal components from each such source. In particular, as noted above, signals from each discrete source are preferably spatially separated, at least partially, into at least two, and preferably, three, four or even more separate signal components, that are directed onto the detector array and are capable of resolution and ultimately being separately detected. In some cases, two different signals that may be emitted from a given signal source may not be completely spatially separable onto different regions of a detector array. However, because such signals differ in their emission wavelength spectra, subjecting such different signals to the wavelength separation components of the optical train, e.g., a prism such as prism 610 in FIG. 6, can yield imaged signals on a detector array that have imaged shapes that are characteristic of the particular emission spectrum, while not being completely spatially separable from another signal components having slightly different emission spectra. In such cases, identifying the signal component that gives rise to a detectable event can sometimes include identification of a characteristic shape of an aggregate group of pixels upon which such signal is incident. As will be appreciated, in those cases that utilize detector arrays as image detectors, e.g., CCDs, CMOS sensors, and the like, detection of image shape will typically refer to detection of signals at the various detector elements, or pixels, that are reflective of an imaged signal of a given shape. Thus, identifying a signals imaged shape will generally refer to detection of signal at pixels underlying that image shape, rather than holistically identifying the shape. Further, the identification of the signal component based upon the imaged shape may not specifically include a step where the shape is identified, but rather that signal is detected that is characteristic of that shape. Thus, with respect to these methods, identification of image shape may not include any step whereby the shape is actually identified, e.g., "shape is circular", but may only be identified by the identification of the pixels upon which the signal is incident.

VI. Data Management

The systems of the invention also typically include a data processing system coupled to the detector for processing and/or recording signals that are incident upon and detected by the detector, and for processing that data to useful information for the user. For example, in the case of single molecule analyses, e.g., where the signal source comprises fluorogenic reactants, the data processing system may assign a value to the incidence of signal on a given location of the detector at a particular time, as being indicative of the occurrence of a given reaction. The data derived from each signal would typically include one or more of (a) the intensity of the signal, (b) the pixel or pixels upon which the signal was incident, (c) relative time that the signal was detected, and the like. Such data may then be processed to indicate relative rates or activities of reactants, order of reactions, a particular signal source from which the signal was derived, and through knowledge of that source's reactants, the nature of an analyte exposed to such reactants.

For ease of discussion, where the signal source includes template directed DNA synthesis using fluorescent nucleotide analogs and DNA polymerase enzyme within an optical confinement, a signal may be indicative of the incorporation of a nucleotide at a given relative position in the synthesis. Further, using the spectral separation aspects of the optical train, and four different nucleotide analogs all bearing dyes or labels having resolvably different spectral characteristics, e.g., that are separated by the optical train and directed to different locations on the detector (or that possess different imaged shapes) as a result of their differing spectral characteristics, a signal at a given location on the detector (or having a given shape) can be indicative of incorporation of a specific type of analog, and the relative timing of such signal would be indicative that such base occurs in the template sequence before or after another base which gave rise to an earlier or later signal, respectively. Finally, the location on the array where such signals are incident is indicative of the signal source from which the signals derive (e.g., indicating that subsequent signals at the same approximate location (subject to, e.g., spatial separation based upon spectral differences of components of signals from a given source) are likely a result of the continuation of the same reaction). This detection is repeated multiple times to identify the sequence of incorporation of multiple nucleotides. By virtue of the complementarity of incorporation in template directed DNA synthesis, one may then ascertain the underlying sequence of nucleotides in the template sequence.

In at least one aspect, as with the aspects of the invention that adjust the array of sources depending upon expected optical aberrations, one may also adjust the methods by which data is acquired and/or assigned to individual sources, based upon those expected optical aberrations. In particular, as noted previously, an amount of distortion of an imaged array can increase as a function of distance from the axial center of the object field. As a result, correlating or assigning individual pixels or groups of pixels to a specific signal source in an imaged array becomes more difficult away from the center of the image. Additionally, optical aberrations may further deform the shape of the imaged signal depending upon the position on the detector array of the imaged signal. For example, certain optical aberrations, i.e., coma, may yield an imaged signal from a circular source that is 'tear-drop' shaped, falling away from the axial center of the imaged field. Alternatively, combinations of astigmatism and field curvature could result in an elliptical signal image shape from a circular signal source, which is more pronounced with increasing distance from the axial center of the object field.

Figure 11:
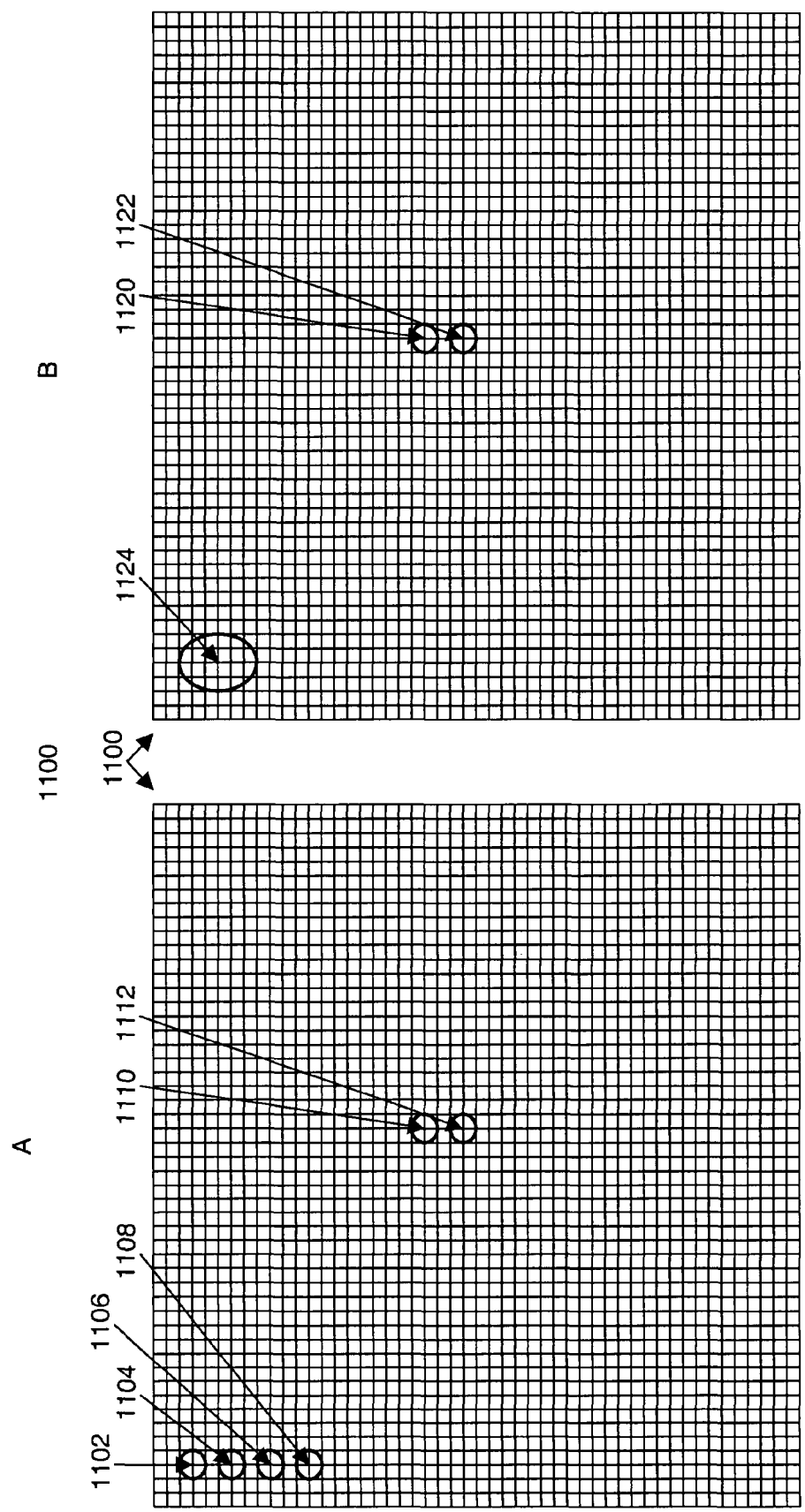
FIG. 11 provides a comparative illustration of signal image correlation methods from a detector array that take into account optical aberrations in the upstream optical train.

Accordingly, in at least one aspect, one can accommodate increasing levels of distortion by expanding the number of pixels that are correlated to any given source, in conjunction with a known or expected optical aberration of the system. In a simple form, this involves increasing the number of pixels correlated to a given source being imaged as that image (or its respective image source) is farther away from the center of the image or object field. A schematic illustration of this is shown in FIG. 11. As shown, an array of pixels in an array detector, e.g., a CCD 1100, is provided to image the array of signal sources. As shown in panel A, in the absence of optical aberrations, uniform signal sources yield uniform images upon the CCD, e.g., as indicated by signals 1102-1112, regardless of where in the image field they emanated from. However, in the case of systems sensitive to such optical aberrations, as the distance increases between the center of the imaged field and a given imaged source, e.g., moving from imaged spots 1120 and 1122 to spot 1124, the distortion results in increasing image size, and/or lower resolution. In order to account for this distortion, the pixels correlated to a given image or signal are increased to maximize the data acquired for each imaged signal, e.g., by acquiring as much of the given signal as possible or practicable, e.g., including all of the different pixel regions at the center and periphery of the object field, imaged onto the CCD. The adjustment of correlated or recorded pixels for any given signal image is a particularly useful process when combined with an array of sources that is further arranged to account for such optical aberrations, e.g., see FIG. 3, above. Alternatively, or additionally, and also as shown in FIG. 11, one may adjust the assigned pixels for a particular imaged signal to account for distortions in the shape of the imaged signal, e.g., for an elliptical or tear-drop shaped image. In particular, one may employ a collection of pixels for an individual imaged signal that is larger in one axis than the other, e.g., longer in the y axis as shown in FIG. 11.

In addition to the improved ability to separately monitor signals from discrete sources, the use of such CCD or other array detectors provides additional benefits for analysis of signals from the individual signal sources as well as the aggregate signals from the overall array of signal sources. For example, where a signal from a given discrete source is incident upon multiple pixels, the compartmentalization of data on a pixel basis allows selection of optimal pixels in a given imaged signal, for data analysis, e.g., eliminating edge signals that may have higher levels of noise or distortion. Additionally or alternatively, pixels used to obtain signal data for each discrete signal source may be individually tailored for a variety of different purposes, as discussed elsewhere herein. The management of such pixel data is further described in greater detail below.

In addition to accommodating and/or correcting for optical aberrations, the present invention also provides processes that provide more efficient processing of relevant signals. In at least one general aspect, such processes involve the further processing of only relevant signals, while either discarding or combining less relevant signals. In either case, by reducing the amount of signal data that is subjected to the full range of further processing, one can speed up that processing, reduce processing requirements, e.g., computing power, reduce real estate on an array detector required for image data management, extend the lifespan of detector components, and achieve a variety of other benefits. These processes generally may be carried out either in the context of the CCD chip, or they may be performed in a subsequent, off-chip processes, e.g., using a computer. As will be appreciated, in many cases, preferred implementations are carried out within the image data processing steps on the detector array itself.

In the context of the present invention, it will generally be understood that the term "processing" refers to automated processing of data by a mechanical or solid state processor or system that is programmed to carry out such processes, e.g., in machine readable software or firmware. Thus, the processing steps may be carried out by a single solid state device, e.g., an appropriately configured detector chip such as an EMCCD, or by a connected or integrated computer or other processor.

As alluded to above, in certain aspects, the invention provides for an initial data processing or selection step to avoid the management, storage and/or processing of excessive irrelevant data that is or would be produced by the detection system, as well as the combined processing of certain data from different areas on the detector. In particular, in some cases, one may gain significant advantages, e.g., in terms of speed of data processing and management and usefulness of background signal data, through the selective skipping, removing, or combining of pixel data prior or subsequent to extraction of data, e.g., from a CCD chip. Stated in another way, by ignoring or separately processing data collected from certain pixel areas that do not contain highly relevant data, e.g., they fall outside of a relevant imaged signal, one can speed up the data management process by removing large amounts of irrelevant data from the process or combining into one processible unit, all of the background or less relevant signal data. Additionally, or alternatively, such combined less relevant pixel data may be useful to derive more meaningful background signal levels, or noise, of the system. In either case, the speed and accuracy of the system should benefit.

By way of example, where one is imaging a large number of discrete signal sources or separated signals derived from such sources, on a single detector array, e.g., a CCD, ICCD or EMCCD, space between imaged signals from such discrete sources gives rise to little or no useful data, as it is a "quiet" space. Notwithstanding the lack of useful signal data emanating from these regions of the detector array, the data from such locations has typically been recorded, e.g., as a zero, or some other low level signal value, or other irrelevant value. While such signals can be disregarded as background, their recordation and processing to the point of discard still requires memory space for storage and processing capacity for evaluation and ultimate discard. Accordingly, in certain aspects, the invention provides a masking process for filtering out such quiet locations on the detector array, and thus blocking the data from being recorded.

Figure 12:
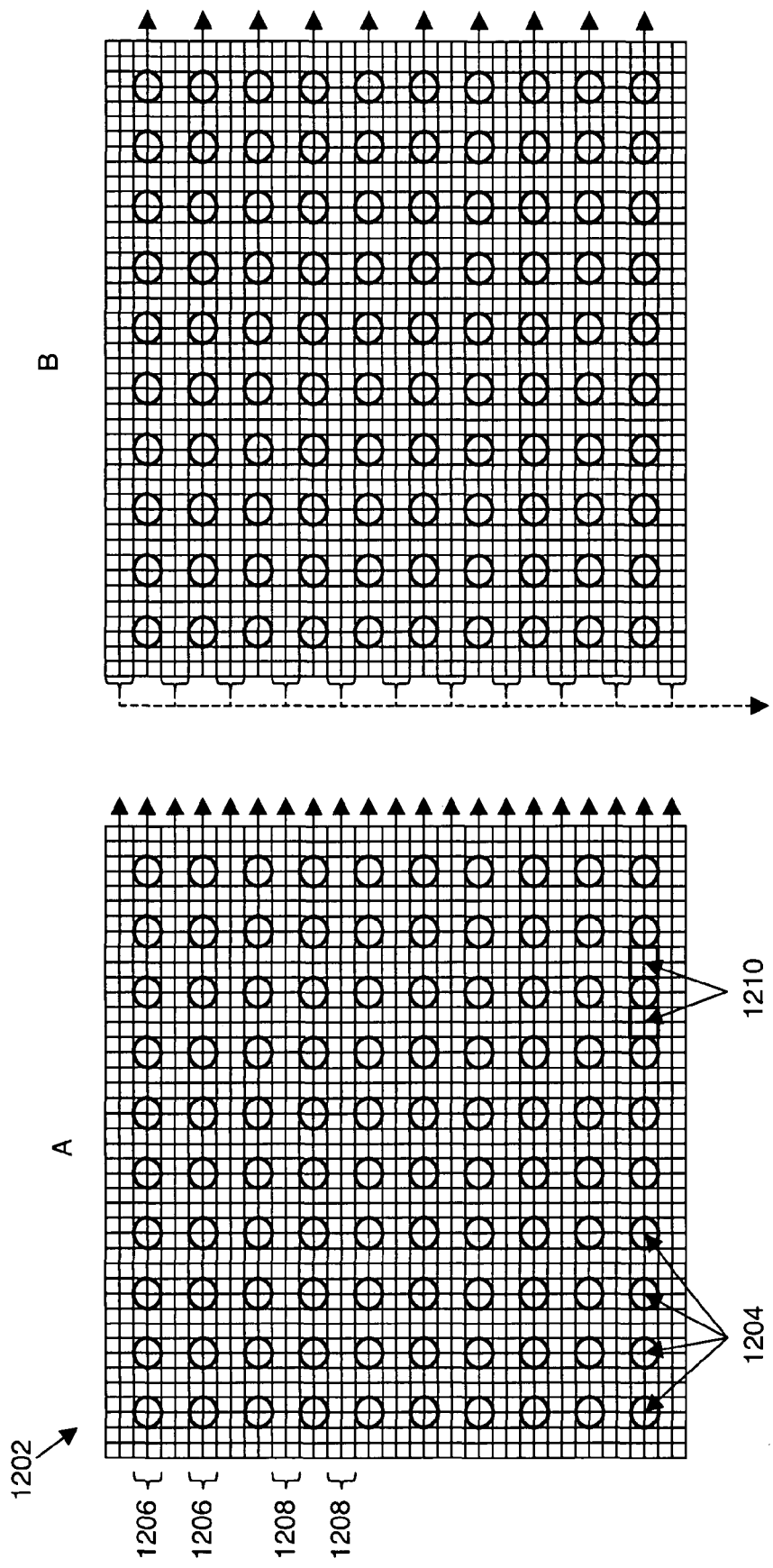
FIG. 12 schematically illustrates a comparison of data extraction processes in conventional image processing versus processes employed in certain aspects of the invention.

For example, in a first aspect, rows of detector array elements, such as pixels in CCD based detectors, that fall between rows of imaged signals from the discrete signal sources, and thus carry signals that are not as relevant to the desired analysis, may be skipped during data extraction from the detector arrays. FIG. 12 provides a schematic illustration of this data extraction profile in a CCD array. As shown, individual signals 1204 from signal sources (not shown) are imaged onto an array detector, e.g., CCD 1202. As shown, the imaged signals 1204 are imaged upon rows of pixels 1206 that are interspersed with rows of pixels 1208 upon which no relevant signals are being imaged, also generally referred to as "quiet pixels". As will be appreciated, within each row of pixels 1206 upon which are imaged relevant signals, there may exist quiet pixels between each individual imaged signal element, e.g., pixels 1210. For ease of illustration and discussion, the extraction of data from pixel rows and/or columns is generally illustrated with respect to pairs of adjacent rows and/or columns, rather than from individual pixel rows, but such illustration is not indicative of any process requirement or other parameter.

In a typical image extraction process, all of rows 1206 and 1208 would be subjected to the same processing steps, resulting in a substantial amount of resources being dedicated to the processing of the less relevant or quiet pixels. This is schematically illustrated by the arrows emanating from each pixel row (or pair of pixel rows, as shown), e.g., relevant signal rows 1206 and quiet pixel rows 1208.

In accordance with certain aspects of the invention, and as shown in the image in panel B, however, data is extracted from the pixels, e.g., the rows and/or columns that carry imaged signals, e.g., rows 1206, from an array of signal sources, while the intervening rows and/or columns, e.g., rows 1208 (and optionally quiet pixel columns that include, e.g., pixel regions 1210) are ignored from a data extraction standpoint. This is shown in FIG. 12, panel B.

In particular, as shown, an application of the process would involve skipping extraction of data from rows 1208, while extracting data from rows 1206. While data from the analyzed rows is subjected to further processing, e.g., passed through EM gain register and/or the analog-digital converter (ADC), to the computer or processor for subsequent storage and manipulation, the skipped rows are not. This effectively reduces the amount of data that is run through the ADC by more than half, in the example shown. Alternatively or additionally, the data derived from rows 1208 may be separately combined and/or averaged prior to or subsequent to extraction (shown by the dashed arrow in panel B) to provide a more significant determination of background noise levels of the system, which may then be used to further correct the signal data extracted from, e.g., rows 1206. Even with such processing of the quiet pixel data, by binning this data together for processing in a single processible data unit, the efficiencies described above are largely retained.

In other aspects, data from related array elements may be combined or "binned" before being subsequently processed, in order to minimize the number of separate data elements that are subject to processing. For example, with reference to the extracted row data described above, each set of rows and/or columns that corresponds to a particular signal source image, or the space between imaged signal sources, may be separately binned for subsequent processing, reducing the number of data elements that are subjected to processing. Similarly, pixels corresponding to images from individual signal source array elements may be binned together and processed. In each of the foregoing cases, whether alone or in combination, the overall number of data elements is substantially reduced over the extraction and processing of each individual pixel element.

In addition to providing benefits of data management selectively binning pixels of imaged signal components may provide advantages of data analysis. For example, when imaging spatially separated signal components, one can selectively bin those elements that are derived from signal rows that are of similar fidelity, allowing subsequent identification of lower fidelity signals, in aggregate. As noted previously, in certain embodiments, the constituent elements of each signal, e.g., the different signal wavelengths emanating from each signal source, are subjected to spatial separation and are imaged onto different pixels, or collections of pixels, on the detector array. As will be appreciated, because constituent signal wavelengths tend to fall over a range rather than within a precise single wavelength or wavelength range in some cases, and because addition of more signal wavelength components within the signal sources as may occur with various applications and/or multiplexing, spatial separation may yield less than complete separation between different signal constituents along each row, e.g., resulting in spectral overlap of the separated signals.

In accordance with certain aspects of the invention, data that is of higher fidelity is processed separately than lower fidelity data, even within an imaged signal. In its simplest sense, only pixels that correspond to the highest fidelity data, e.g., having the highest intensity relative to a noise level of the system, are processed as relevant signals. Other signal components are then subjected to different processing or are discarded. In general, as will be appreciated, such signal components are those that are within the main portion of the imaged signal, e.g., toward the center of the imaged signal, rather than at its periphery. An example of this is illustrated with reference to FIG. 13A which shows a representation of an imaged signal 1300 upon a set of pixels 1302 in an array detector. In accordance with the signal selection processes described herein, only those signals derived from pixels at or near the central portion of the imaged signal, e.g., pixels in region 1304 (shown without hatching) are subjected to processing as relevant signal data. Signals from pixels at the periphery of the signal, e.g., pixels in region 1306 (shown cross hatching), would be expected to be of lower fidelity, e.g., having lower signal to noise ratios. Accordingly, pixels in region 1304 are subjected to processing as relevant signal while pixels in region 1306 are treated separately which may include discarding or inclusion in determination of an overall system signal to noise ratio. As will be appreciated, the selection of higher confidence signal data or their respective pixels may be carried out by a number of parameters including without limitation, selection of higher intensity signals within an overall imaged signal, and/or selection of signals that are expected to be of higher confidence based upon their position in an overall imaged signal, e.g., they fall within a central portion of the overall imaged portion, where the central portion refers to a signals from a subset of pixels impinged upon by the overall imaged signal, while pixels that are within the overall imaged signal, but fall at the periphery or around the entire edge of the imaged signal, are discarded. For generality, it could be viewed that the signal portion that extends only a portion of the radius of the overall imaged signal, would be viewed as of high confidence, where that portion may vary from, e.g., 25%, to 50% to 75% or even 90% where signal images are highly coherent.

Figure 13B:
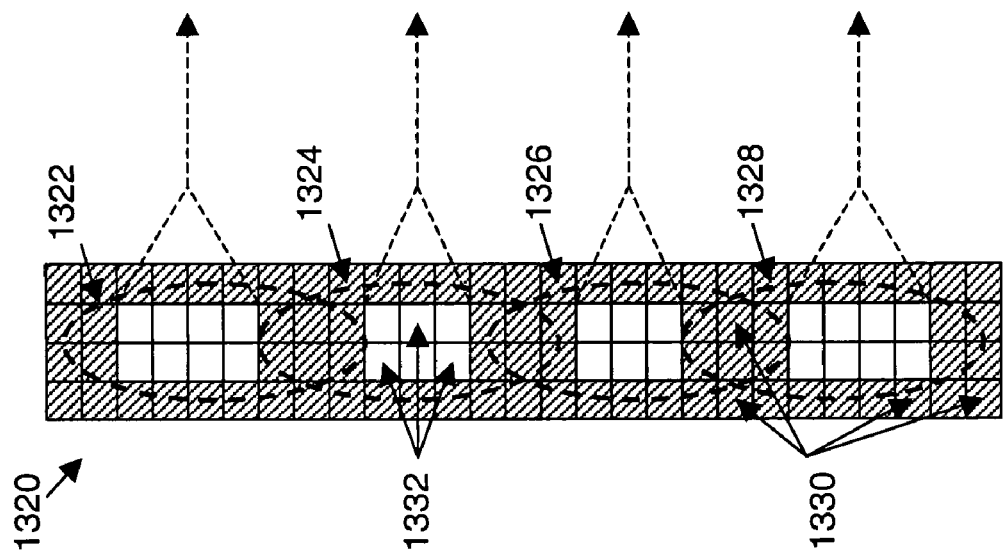
FIGS. 13A and B schematically illustrate pixel correlation to imaged signals or signal components to improve the fidelity of data from a given image or set of images.
Figure 13A:
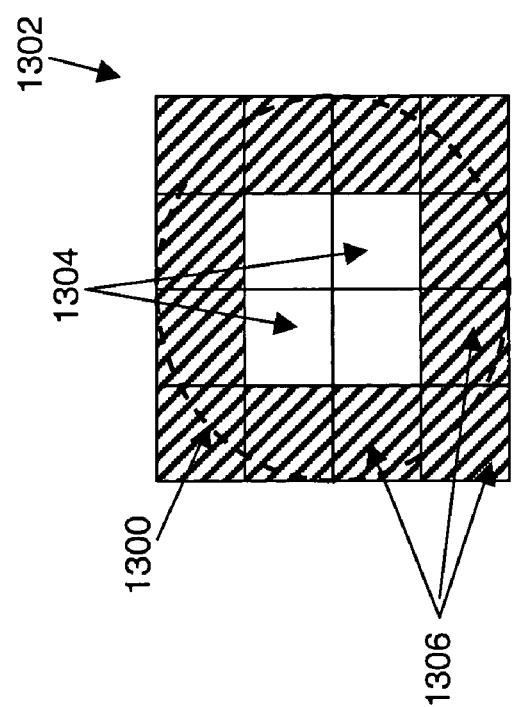

A more complex implementation of this selection process, where a signal from a given source is spatially separated with incomplete separation, e.g., with substantial signal overlap, is shown in FIG. 13B. As shown, a signal is imaged upon a set of pixels 1320 in an overall detector array. As shown, the signal is subjected to spectral separation whereby signal components having different spectral characteristics are directed to different (albeit overlapping) groups of pixels on the array. This is illustrated by signal images 1322, 1324, 1326, and 1328 which show considerable overlap. In accordance with this aspect of the invention, less relevant pixels, such as those that are at the periphery of each signal component or are occupied by overlapping signals, such as pixels 1330 (shown cross hatched), are discarded prior to, or combined for processing. Meanwhile, high fidelity signals upon, e.g., pixels 1332 (shown without hatching) are subjected to further processing as relevant signals.

In accordance with the processing aspects of the invention, relevant data, e.g., from pixels 1332, from each signal, e.g., signals 1322-1328, can be binned together for each signal component and processed as shown by the dashed arrows, e.g., passed through the EM gain register, the A/D conversion, and subsequent processing by the computer. All other, lower fidelity data surrounding the signals, as well as that which is included in the signal overlap regions (e.g., pixels 1330, may be discarded or binned together for simultaneous processing, e.g., A/D conversion, inclusion in background signal calculation, etc.

By binning the lower fidelity data, e.g., that includes excessive levels of mixed signal constituents, one can effectively discard or process all of these signals simultaneously, or at least separately from the relevant pixel data. In accordance with certain aspects of the invention, the data is binned in a manner that combines each set of pixels that includes the same level of spectral overlap (or absence thereof), as shown by arrows 1334 and 1336. As with the quiet detector spaces referred to previously, data from the pixels that fall between the pixels having the highest fidelity signals may be processed separately from the high fidelity signal data. For example, it may be discarded prior to subsequent processing, or it may be binned and processed in merely a separate process operation from the high fidelity data. Alternatively, it may be combined with all other low fidelity data, to generate a background level of spectral overlap signal, or the like.

In accordance with the foregoing and other aspects of the invention, it will be appreciated that rows or columns of pixels may include rows or columns that range from a single pixel width to 2 or more, 5 or more, 10 or more, or 100 or more pixels in width, or any pixel width that falls within these ranges. The specific number of pixels that fall within a given row or column, whether it be a signal row or column or a "quiet" row or column, will depend upon the desired application, and they may be varied from system to system, or even within a given system, e.g., column and row widths in the monitoring of any given substrate may vary across the detector, e.g., one signal row may be two pixels wide while another row is 10 pixels wide. Likewise, in the same application, while a given quiet row may be 2 or 10 pixels wide, another quiet row in the same detection event may be 10 or 20 pixels wide.

Further, any of these signal data manipulation techniques may be applied dynamically, to optimize different parameters, e.g., signal to noise ratio, for each analytical operation that is being performed. In particular, one could adjust the relative spacing of the excluded rows and/or columns, the number of pixels being assigned to each signal event, or any combination of these to achieve a desired signal to noise ratio, e.g., by comparing a standard signal to a background noise. Further, this could be performed using appropriate software programming to be able to optimize for any of a number of different regions or numbers of regions or signal sources imaged onto an array.

In some cases, it may be desirable to provide a physical mask over an array detector to filter any signal derived from areas between the signal sources spaces on the detector array to filter out any noise derived from signal in adjoining signal sources/pixel areas. The physical mask may comprise a separate optical element, e.g., an opaque substrate having optical apertures disposed at regions that correspond with the imaged signals, e.g., similar to photolithographic masks used in semiconductor fabrication. Alternatively, the mask may be provided as a layer over the detector array, e.g., using light absorbing polymers or polymers containing light absorbing materials, photoresists, or the like.

As will be appreciated, noise that derives from the system itself, and that will still be present in the event that a mask is used without other adjustments, may be accounted for and dealt with in any of the methods described above. In a further aspect, one could employ detector arrays that are specifically configured, e.g., through the placement of detector elements, e.g., pixels in a CCD, to correspond to the regions upon the array where signals will be incident, and thus exclude background signal events, e.g., that would be incident on the array between relevant imaged signal events.

In at least one aspect of the invention, a modified EMCCD is used as the detector array. In particular, and as schematically illustrated in FIG. 10, conventional EMCCDs use a frame transfer process in moving data to the storage area of the CCD chip, and then use a separate EM Gain register to provide signal gain of up to 100×, 500×, 1000×, 2000× or more before the data is digitized and transferred to the processor, e.g., a connected computer. While this process is effective in the detection of low light level signals, the separate EM Gain register can be quite large, relative to the overall chip footprint, occupying a great deal of CCD chip real estate. In accordance with certain aspects, the EMCCD is configured so that the clocking voltages used for the row shift process are arranged to realize the gain during the transfer of data from the image area to the storage area, rather than post storage via an EM Gain register. In particular, as noted previously, typical frame transfer process to the storage area on the CCD chip, and subsequent transfer to the EM gain register are each carried out with an applied potential of approximately 2V. Processing the charge associated with the signal through the gain protocols in the EM gain register is then done with an applied potential of approximately 50V. By applying the 50V and implementing the gain protocol during the frame transfer process, one can obviate the need for the EM gain register.

In addition to the foregoing, and as further examples of the benefits of the invention, current EMCCD cameras operate by adding a long string of "pixels" (several hundred) and applying a very high voltage (50V or more) to move the data from one pixel to the next. 50 V is sufficient to cause a small probability of creating spurious charges—for example if one electron is being moved from one pixel to the next, there is a 1% chance that an extra electron will be created, thus doubling the apparent signal strength. Simple statistics can be used to show that a gain of 1000× can be achieved with a 1% probability per pixel and approximately 400 pixels. The drawback of this approach is that there is typically only one gain amplifying channel for the entire EMCCD chip—this means that data from every single pixel must be funneled through the same gain amplifier. In a particular exemplary EMCCD camera, the data is passed through this single gain amplifier and then digitized at a rate of 10 Megahertz, meaning a maximum frame rate of the camera is 33 Hz (512×512 pixels divided by 10 Megahertz).

In the context of the invention, however, applying a higher voltage to the frame transfer process, e.g. similar voltage level to that used in the gain amplifier of conventional EMCCDs, one could attain similar or greater amplification. Further, and with reference to an exemplary EMCCD chip having 512 rows of pixels (512×512), the frame transfer process would include 512 transfers from one pixel to the next. A voltage less than 50V, with a probability a bit less than 1%, would provide the 1000 gain that is available through a integrated gain register. As a result of negating the need for a gain register and its associated bottle neck and chip area requirements, the EMCCD according to the instant invention would be much faster, and the real estate required could be about half, which would be expected to cut the chip cost in half.

Thus, in certain aspects, the invention includes methods for processing image data from a CCD, and particularly an ICCD or EMCCD, that include applying gain voltage during a frame transfer process, and CCD based detectors that are configured to carry out this process. By utilizing the frame transfer process as the gain amplification process, one significantly increases the processing speed for signal data, significantly reduces the chip real estate, and consequently the chip cost associated with a typical EMCCD camera or other such detector.

Another aspect of the signal image data processing aspects of the invention provides benefits in terms of preservation of system performance, in addition to providing advantages in efficiency of data processing. In particular, as noted above, CCD detectors, and particularly, high sensitivity CCDs, such as EMCCDs are preferred for use as detector arrays in the systems of the invention, because they can offer a combination of high gain, parallel readout and fast framerate. These attributes make such detectors particularly well suited for use in applications that are temporally monitoring operations that yield very low level optical signals, such as single molecule analyses. However, as a result of possessing these attributes, the EMCCDs may be subject to degradation of performance. In particular, in the case of EMCCDs, the EM gain register may be subject to rapid degradation when large amplitude signals are passed trough it.

In preventing such degradation, it is generally desirable to limit the amplitude of signals being processed by the EM gain register. However, even limiting such amplitudes to within manufacturer recommendations still can yield substantial degradation. Without being bound to a particular theory of operation, it is believed that a contributing factor to gain degradation is the combination of signals on the CCD chip, when a subset of pixels of the array in a region of interest on an array is read out from the chip. This operating mode can be implemented differently on different EMCCD configurations, but for at least some configurations, the pixel rows that are outside of the region of interest are combined together and then passed through the EM gain register. This can lead to substantial variation in the amplitude of the signals being passed through the register, leading to degradation. Accordingly, the present invention also provides methods for reducing or eliminating the large amplitude variation of signals being processed by the gain register.

In certain aspects, this is achieved applying the processes described elsewhere herein. In particular, the excess charge that derives from regions of the CCD that are not used to image relevant signals, e.g., those regions of the CCD that fall between or outside imaged signals from signal sources, are cleared before passing the overall signals through the gain register. In particular, a number of EMCCD configurations are available e.g., EMCCDs from E2V Technologies, Inc., that include electrical taps that may be used to bypass the gain register and send the signal output from these other regions to a separate destination, e.g., as shown by the dashed arrow in FIG. 12, panel B, but leading to a separate output from the EM gain register. These taps may be configured on a per frame basis, and may, along with the control pins, be integrated into the CCD design.

In an alternative or additional method, and as alluded to above, one may also only subject certain highly relevant array regions to subsequent processing, e.g., disregarding regions where little or no relevant signal is imaged, e.g., spaces between or surrounding relevant signal regions on the array. By avoiding passing data from these regions through the EM Gain register, at least one source of large amplitude variations, e.g., the variation from relevant signal bearing pixels and pixels that are just communicating noise, in the signal data can be avoided. This is generally accomplished by providing for a readout of the chip on a segmented basis, e.g., pixel by pixel, or sub-region by sub-region. This is a particularly useful solution where the imaging frame rate is not required to be fast, e.g., greater than 33 Hz, allowing for the slower processing methods.

Figure 14:
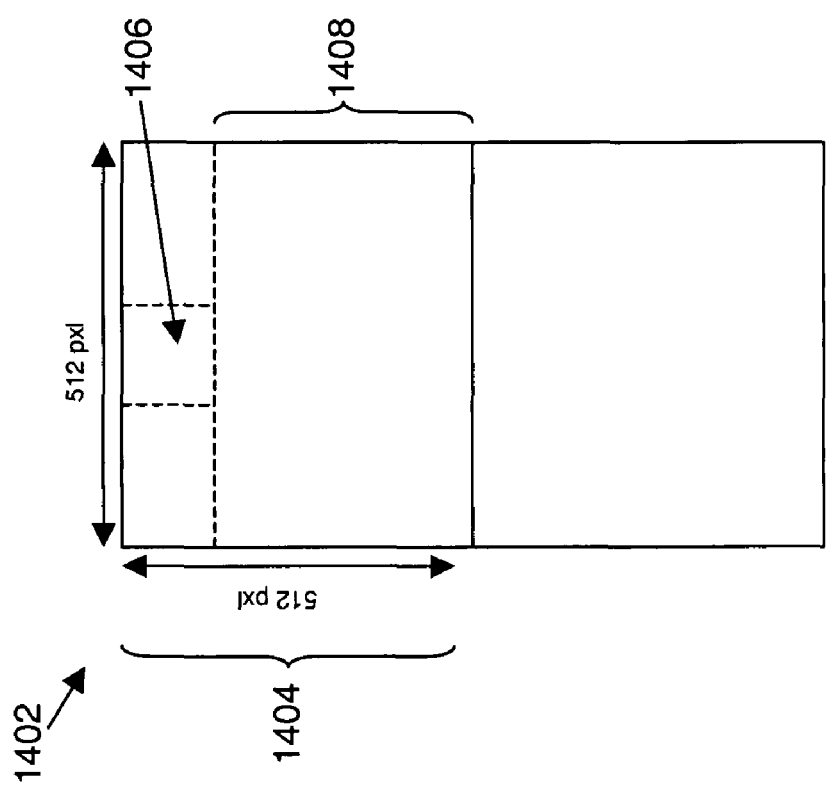
FIG. 14 schematically illustrates data management on an EMCCD detector to enhance efficiencies of the system.

For higher framerate applications, the charge combination effect can be mitigated by reducing the number of rows that can be combined together. For example, and with reference to FIG. 14, in a 512×512 pixel EMCCD 1402, where within the image area 1404, an 80×80 sub-region 1406 is read out, over up to 432 rows of irrelevant or quiet pixels 1408 can be combined together. If these rows are combined in groups of ten, instead of as a single group, the damage effect will be reduced by a factor of 43, while maintaining a relatively high framerate, e.g., 100 Hz or greater.

Figure 15:
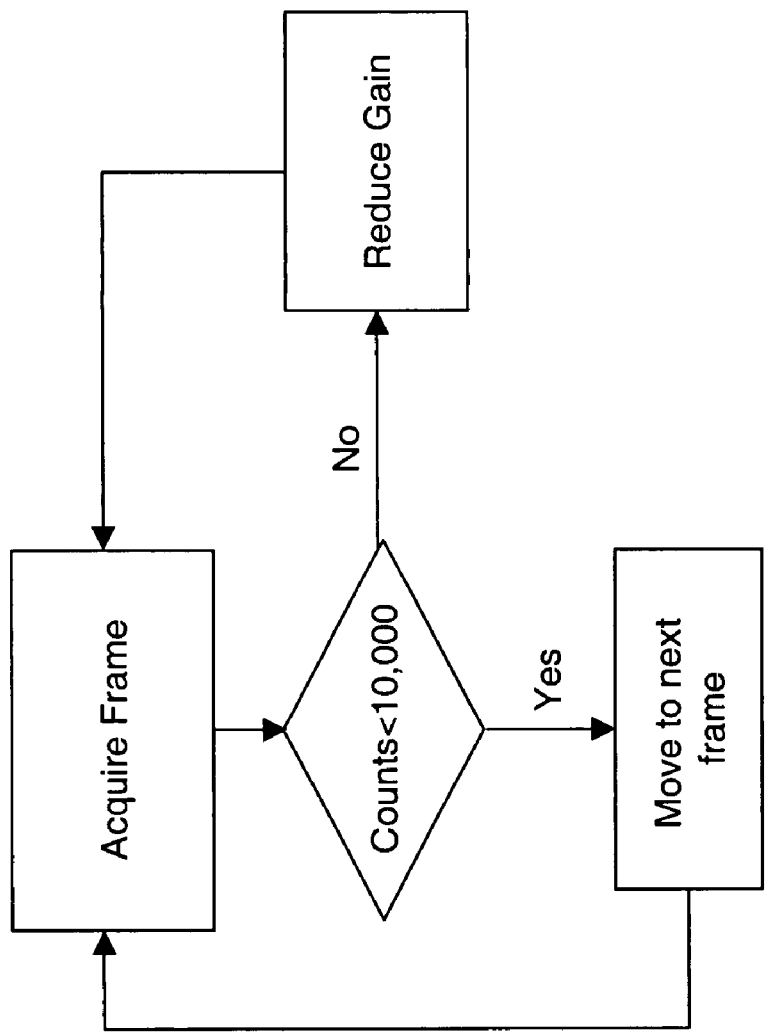
FIG. 15 provides a flowchart of data processing from CCD detector arrays to minimize effects of large signal variations.

In yet another aspect, a CCD may be programmed to adjust the EM gain, dynamically as it recognizes large signal amplitude variations. In such applications, the voltages of the EM gain register would be reduced when processing charge from outside of the region of interest on the array. Alternatively, software can be implemented to monitor the maximum signal, and reduce the EM gain automatically when that signal exceeds a proscribed level. This is schematically illustrated in the process flow chart provided in FIG. 15. This can also be extended to signal packets that come through the EM gain register. Finally, masking techniques, e.g., knife edge masks, can be employed to mask off rows on the CCD that are outside of the regions of interest that would otherwise be combined.

Relatedly, the detectors and/or systems of the invention may provide for the automatic measurement and/or calibration of the gain, by automatically determining the gain in the absence of actual signals. In particular, in many multiplying image detectors, such as EMCCDs, degradation of gain over time can create issues of signal and data quality, unless the gain is regularly measured and calibrated, so as to provide amplified signal data within a desired range. In the past, this measurement has been carried out manually, requiring significant time and effort, and introducing potential avenues for human variation into an overall process.

In accordance with this aspect of the invention, the gain is measured during a period where no signal data is incident upon the detector. Typically, this may be accomplished by automatically closing the shutter of the optical system so as to block signal data from impinging on the detector. Likewise, this could be accomplished by turning off any light sources that might provide such signals. In any event, the gain measured in the absence of signal is then used to calibrate the gain register so as to fall within a desired gain range, and/or to provide signal data that will fall within a desired amplified signal range. These processes may generally be programmed into the controlling computer, e.g., that initiates closure of the shutter, records measured gain and recalibrates gain register.

Although described in some detail for purposes of illustration, it will be readily appreciated that a number of variations known or appreciated by those of skill in the art may be practiced within the scope of present invention. To the extent not already expressly incorporated herein, all published references and patent documents referred to in this disclosure are incorporated herein by reference in their entirety for all purposes.

What is claimed is:

1. A method of monitoring a plurality of spectrally distinct optical signals from a source of optical signals, comprising:
    passing the plurality of optical signals through an optical train that is configured to image each of the plurality of spectrally distinct optical signals onto an imaging detector that comprises a plurality of pixels, wherein an image of each spectrally distinct optical signal produces a shape of an aggregate group of pixels that is characteristic of the optical signal's spectral characteristics;
    imaging the plurality of optical signals onto the imaging detector; and
    identifying each optical signal by the shape of the aggregate group of pixels characteristic of that optical signal.

2. The method of claim 1, wherein the plurality of spectrally distinct optical signals comprises at least two different fluorescently labeled compounds in the source of optical signals, each different fluorescently labeled compound having a different emission spectrum when exposed to excitation radiation.

3. The method of claim 1, wherein the plurality of spectrally distinct optical signals comprises at least four different fluorescently labeled compounds in the source of optical signals, each different fluorescently labeled compound having a different emission spectrum when exposed to excitation radiation.

4. The method of claim 3, wherein the at least four different fluorescently labeled compounds comprise at least four different fluorescently labeled nucleotides, each different nucleotide being labeled with a different fluorescent label having a different emission spectrum.

5. The method of claim 1, wherein the imaging detector is selected from a CCD, an EMCCD, and ICCD, a CMOS sensor, and a hybrid CMOS/CCD sensor.

6. A system for monitoring a plurality of different optical signals from a source of optical signals, comprising:
    a substrate having at least a first source of optical signals disposed thereon, the source of optical signals including a plurality of spectrally distinct optical signals;
    an optical train positioned to receive the plurality of different optical signals from the at least first source of optical signals and differentially image each of the plurality of different optical signals onto an imaging detector that comprises a plurality of pixels such that each of the different optical signals produces a shape of an aggregate group of pixels that is characteristic of the spectrally distinct optical signal;
    the imaging detector that comprises a plurality of pixels; and
    a processor for processing signal data from the imaging detector, wherein the processor is configured to identify the spectrally distinct optical signal by the shape of the aggregate group of pixels characteristic of that optical signal.

7. The system of claim 6, wherein the at least first source of optical signals comprises a reaction region having a plurality of different fluorescently labeled compounds disposed therein, each of the different fluorescently labeled compounds having a distinct fluorescent emission spectrum in response to excitation radiation.

8. A method of monitoring a plurality of spectrally different optical signals from a single signal source, comprising:
    collecting the spectrally different optical signals in an optical train;
    transmitting the spectrally different optical signals through the optical train that is configured to differentially image each of the spectrally different optical signals onto an imaging detector that comprises a plurality of pixels;
    differentially imaging each of the spectrally different optical signals onto the imaging detector to produce a shape of an aggregate group of pixels that is characteristic of the optical signal's spectral characteristics; and
    identifying each spectrally different signal imaged by the shape of the aggregate group of pixels characteristic of that optical signal.

* * * * *